US012700096B2

(12) United States Patent (10) Patent No.: US 12,700,096 B2
Hardingham (45) Date of Patent: Aug. 4, 2026

(54) BRAIN IMAGE PROCESSING

(71) Applicant: OXFORD BRAIN DIAGNOSTICS LTD, Oxford (GB)

(72) Inventor: Ian Hardingham, Oxford (GB)

(73) Assignee: OXFORD BRAIN DIAGNOSTICS LTD, Oxford (GB)

( * ) Notice: Subject to any disclaimer, the term of this patent is extended or adjusted under 35 U.S.C. 154(b) by 270 days.

(21) Appl. No.: 18/291,522

(22) PCT Filed: Jul. 21, 2022

(86) PCT No.: PCT/GB2022/051908
§ 371 (c)(1),
(2) Date: Jan. 23, 2024

(87) PCT Pub. No.: WO2023/002202
PCT Pub. Date: Jan. 26, 2023

(65) Prior Publication Data
US 2024/0346657 A1      Oct. 17, 2024

(30) Foreign Application Priority Data
Jul. 23, 2021      (GB) ...................................... 2110643

(51) Int. Cl.
G06T 7/00          (2017.01)
A61B 5/00          (2006.01)
(Continued)

(52) U.S. Cl.
CPC .......... *G06T 7/0014* (2013.01); *A61B 5/4064* (2013.01); *G06T 7/74* (2017.01);
(Continued)

(58) Field of Classification Search
CPC .................... G06T 7/0014; G06T 7/74; G06T 2207/10088; G06T 2207/30016;
(Continued)

(56) References Cited

U.S. PATENT DOCUMENTS 10,262,414 B2 *   4/2019   Nitzken ................... G06T 7/11
11,796,619 B2 *  10/2023   Chance ............ G01R 33/56341
(Continued)

FOREIGN PATENT DOCUMENTS

WO          2016162682 A1    10/2016

OTHER PUBLICATIONS

Fortin et al. "Removing inter-subject technical variability in magneticresonance imaging studies" May 15, 2016. pp. 198-212.
(Continued)

*Primary Examiner* — Bobbak Safaipour
(74) *Attorney, Agent, or Firm* — Meunier Carlin & Curfman LLC

(57)          ABSTRACT

Systems, methods (300), computer program products, and computer readable media for processing images of brains are described. Techniques are described for transforming, into a common space, reference points obtained from at least one image of a reference brain in a first space (302), transforming, into the common space, test points obtained from at least one image of a test brain in a second space (304), determining a position of each of the transformed reference points and each of the transformed test points in the common space (306), calculating a displacement of each of the transformed test points relative to each of the transformed reference points based on the determined positions (308), determining a correspondence between one of the transformed test points and a given transformed reference point based on the calculated displacements (310), and determining a corresponding test point in the second space to a reference point in the first space based on the determined correspondence (312).

29 Claims, 12 Drawing Sheets

(51) Int. Cl.
    *G06T 7/73*         (2017.01)
    *G16H 20/70*     (2018.01)

(52) U.S. Cl.
    CPC ............ *G16H 20/70* (2018.01); *A61B 5/0042*
        (2013.01); *G06T 2207/10088* (2013.01); *G06T*
           *2207/30016* (2013.01); *G06T 2207/30204*
                          (2013.01)

(58) Field of Classification Search
    CPC . G06T 2207/30204; G06T 2207/10081; G06T
        2207/10092; A61B 5/4064; A61B 5/0042;
           A61B 2505/01; A61B 2505/09; A61B
           5/055; A61B 5/1075; A61B 5/1079; A61B
             5/4082; A61B 5/4088; A61B 5/4094;
               A61B 5/7246; A61B 5/7275; A61B
                       2576/026; G16H 20/70
    See application file for complete search history.

(56)               References Cited

U.S. PATENT DOCUMENTS

| | | | |
|---|---|---|---|
| 2007/0019846 A1* | 1/2007 | Bullitt ................... | G06T 7/0014 |
| | | | 382/128 |
| 2010/0259263 A1* | 10/2010 | Holland ................. | A61B 5/055 |
| | | | 324/310 |
| 2011/0218253 A1 | 9/2011 | Lange et al. | |
| 2015/0012466 A1* | 1/2015 | Sapiro .................... | A61B 6/501 |
| | | | 706/12 |
| 2016/0239956 A1* | 8/2016 | Kang ................... | A61B 6/5247 |
| 2017/0032520 A1 | 2/2017 | Nitzken et al. | |
| 2018/0143282 A1 | 5/2018 | Chance et al. | |
| 2019/0117072 A1* | 4/2019 | Pereira ................. | A61B 5/0042 |
| 2019/0370970 A1* | 12/2019 | Kim ...................... | G06T 7/0016 |
| 2024/0293026 A1* | 9/2024 | Livny-Ezer ............ | A61B 5/055 |

OTHER PUBLICATIONS

Borga "Reproducibility and repeatability of MRI-based body composition analysis" May 15, 2020. 11 pages.
Gronenschild et al. "The Effects of FreeSurfer Version, Workstation Type, andMacintosh Operating System Version on Anatomical Volumeand Cortical Thickness Measurements" Jun. 1, 2012. 12 pages.
Bidas et al. "Reproducibility, Interrater Agreement, and Age-Related Changes of Fractional Anisotropy Measures at 3T in Healthy" 2008. 7 pages.
Correia et al. "Looking for the optimal DTI acquisition scheme given a maximum scan time: Are more b-values a waste of time?" 2008. 1 page.
Papinutto et al. "Reproducibility and biases in high field brain diffusion MRI: An evaluation of acquisition and analysis variables" Mar. 8, 2013. 13 pages.
Takao et al. "Effect of scanner in longitudinal diffusion tensor imaging studies" Feb. 2012. 19 pages.
Zhu et al. "Quantification of Accuracy and Precision of Multi-Center DTI Measurements: ADiffusion Phantom and Human Brain Study" Jun. 1, 2012. 30 pages.
Dale et al. "Improved Localization of Cortial Activty by Combining EEG and MEG with MRI Cortical Surface Reconstruction" 1993. 15 pages.
Dale et al. "I. Segmentation and Surface Reconstruction" May 22, 1998. 16 pages.
Fischl et al. "II: Inflation, Flattening, and a Surface-Based Coordinate System" 27 May 27, 1998.
Fischl et al. "High-Resolution Intersubject Averaging and a Coordinate System for the Cortical Surface" 1999. 13 pages.
Fischl et al. "Measuring the thickness of the human cerebral cortex from magnetic resonance images" Jan. 24, 2000. 6 pages.
Fischl et al. "Automated Manifold Surgery: Constructing Geometrically Accurate and Topologically Correct Models of the Human Cerebral Cortex" Jan. 1, 2001. 11 pages.
Fischl et al. "Whole Brain Segmentation: Neurotechnique Automated Labeling of Neuroanatomical Structures in the Human Brain" Jan. 31, 2002. 15 pages.
Fischl et al. "Sequence-independent segmentation of magneticresonance images" 2004. 5 pages.
Fischl et al. "Automatically Parcellating the HumanCerebral Cortex" Jan. 1, 2004. 31 pages.
Han et al. "Reliability of MRI-derived measurements of humancerebral cortical thickness: The effects of field strength, scanner upgrade and manufacturer" Aug. 1, 2006. 5 pages.
Jovicich et al. "Reliability in multi-site structural MRI studies: Effects ofgradient non-linearity correction on phantom and humandata" Apr. 1, 2006. 4 pages.
Reuter et al. "Highly accurate inverse consistent registration: A robustapproach" Dec. 2010. 6 pages.
Reuter et al. "Within-subject template estimation for unbiasedlongitudinal image analysis" Jul. 16, 2012. 6 pages.
Segonne et al. "A hybrid approach to the skull stripping problem in MRI" Jul. 2004. 5 pages.
Andersson et al. "An integrated approach to correction for off-resonanceeffects and subject movement in diffusion MR imaging" Jan. 15, 2016. 31 pages.
Graham et al. "Quantitative assessment of the susceptibility artefact andits interaction with motion in diffusion MRI" Oct. 2, 2017. 15 pages.
Greve et al. "Accurate and robust brain image alignment usingboundary-based registration" Oct. 15, 2009. 5 pages.
McKavanaugh et al "Relating diff usion tensor imaging measurements to microstructural quantitiesin the cerebral cortex in multiple sclerosis" Jul. 29, 2019. 34 pages.
Torso et al. "Detection of Alzheimer's Disease using cortical diff usion tensor imaging" Nov. 11, 2020. 24 pages.
World Health Organization. 2022. 11 pages.
Gibson et al. "A Combined Surface and Volumetric Registration (SAVOR) Framework to Study Cortical Biomarkers and Volumetric Imaging Data" 2009. 8 pages.
Notification concerning informal communications with the applicant in connection to Application No. PCT/GB2022/051908. Oct. 10, 2023.
Combined Search & Exam Report in connection to Application No. GB 2110643.0. Dec. 14, 2021. 6 pages.
International Search Report and Written Opinion in connection to Application No. GB2022/051908. Dated Nov. 14, 2022. 18 pages.
Written Opinion of the IPEA in connection to Application No. GB2022/051908. Jun. 19, 2023. 9 pages.
International Report on Patentability in connection to Application No. GB2022/051908. Oct. 31, 2023. 64 pages.

\* cited by examiner

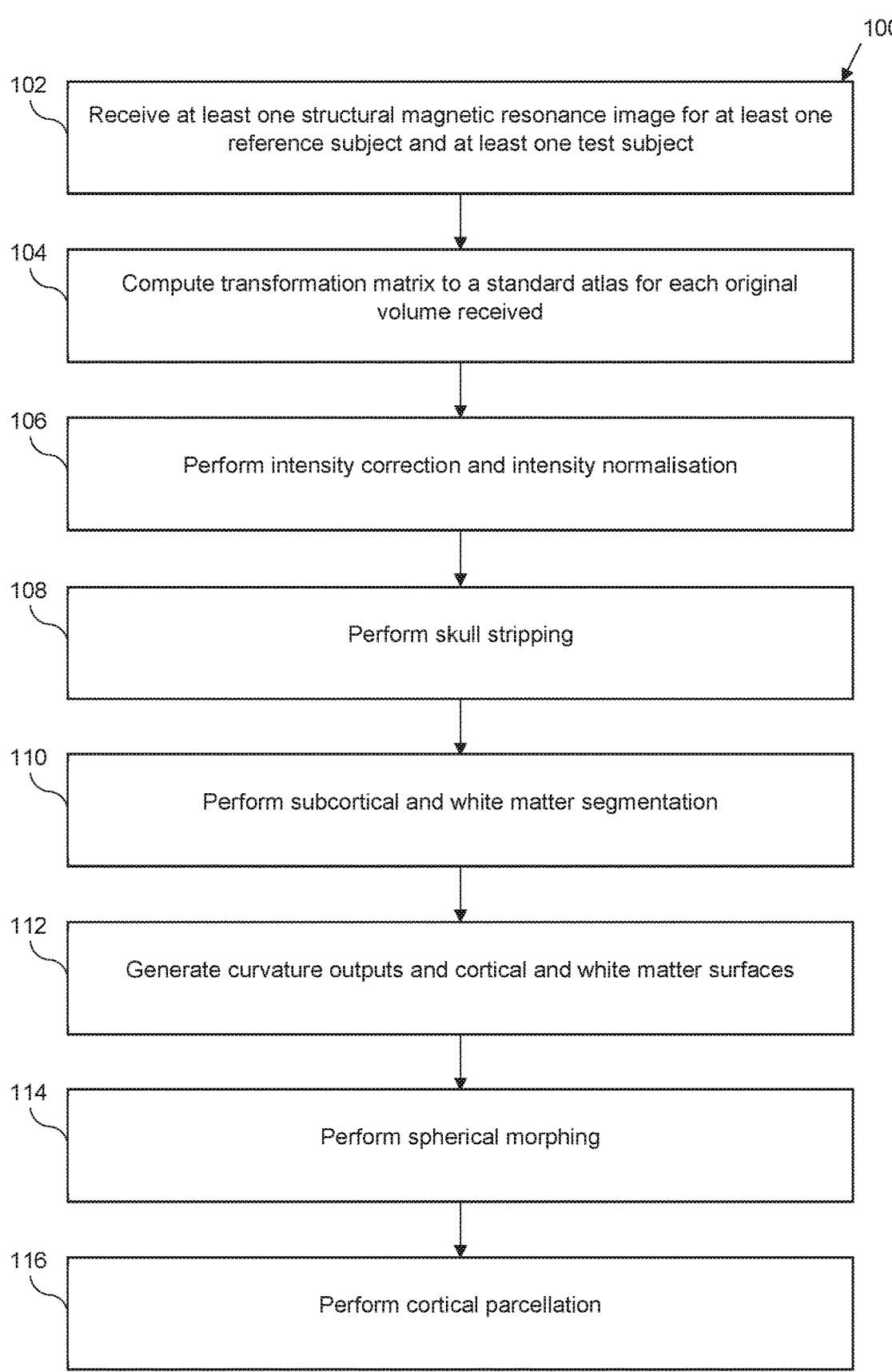

100

102 — Receive at least one structural magnetic resonance image for at least one reference subject and at least one test subject 104 — Compute transformation matrix to a standard atlas for each original volume received 106 — Perform intensity correction and intensity normalisation 108 — Perform skull stripping 110 — Perform subcortical and white matter segmentation 112 — Generate curvature outputs and cortical and white matter surfaces 114 — Perform spherical morphing 116 — Perform cortical parcellation

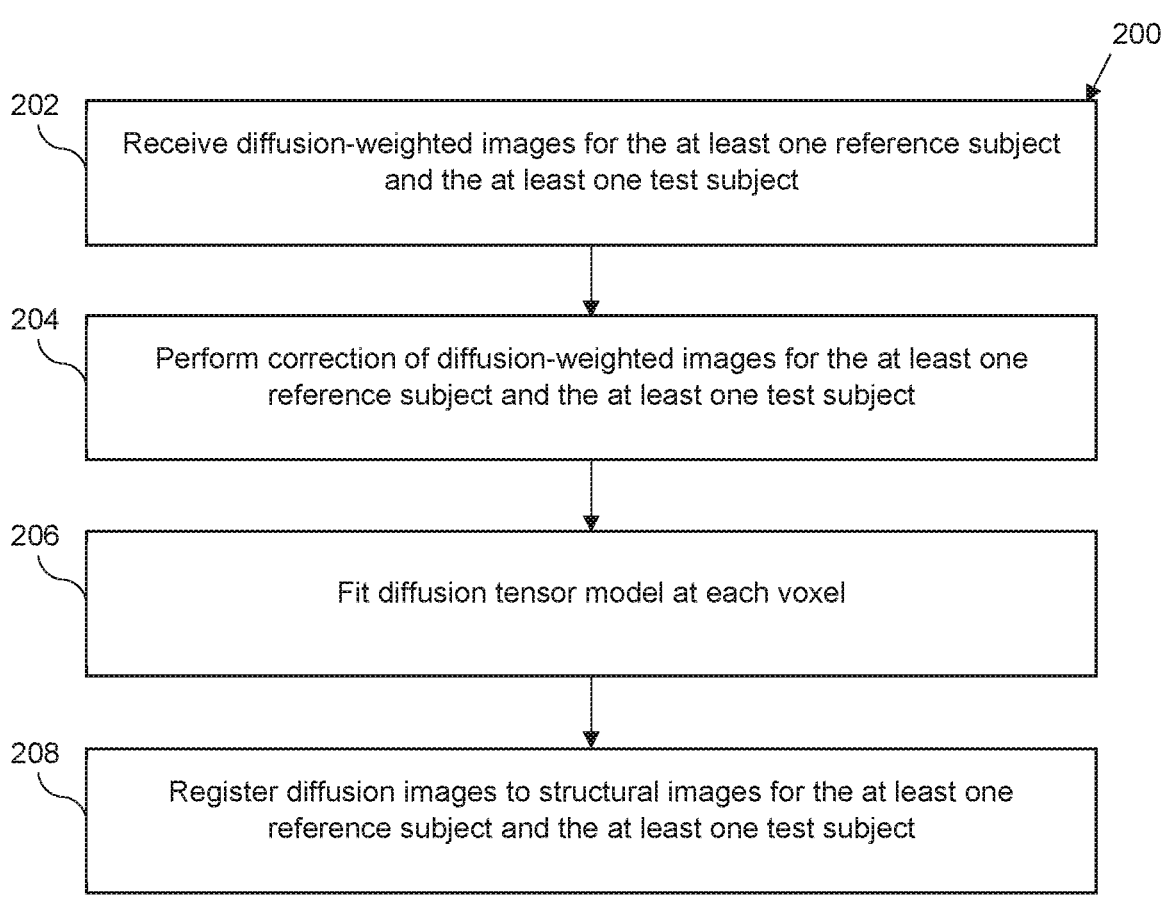

202

Receive diffusion-weighted images for the at least one reference subject and the at least one test subject

204

Perform correction of diffusion-weighted images for the at least one reference subject and the at least one test subject

206

Fit diffusion tensor model at each voxel

208

Register diffusion images to structural images for the at least one reference subject and the at least one test subject

FIG. 2

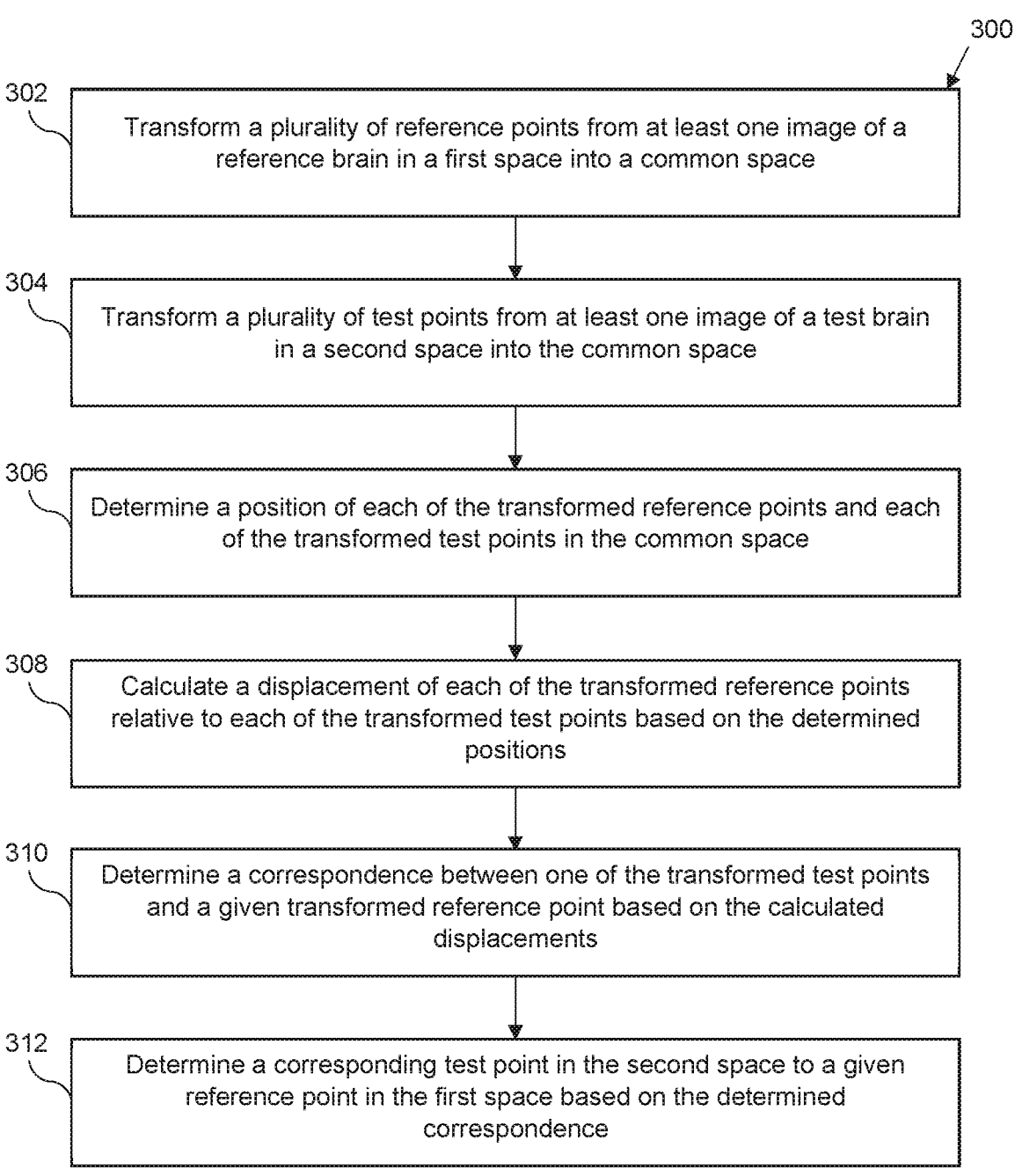

300

302

Transform a plurality of reference points from at least one image of a reference brain in a first space into a common space

304

Transform a plurality of test points from at least one image of a test brain in a second space into the common space

306

Determine a position of each of the transformed reference points and each of the transformed test points in the common space

308

Calculate a displacement of each of the transformed reference points relative to each of the transformed test points based on the determined positions

310

Determine a correspondence between one of the transformed test points and a given transformed reference point based on the calculated displacements

312

Determine a corresponding test point in the second space to a given reference point in the first space based on the determined correspondence

FIG. 3

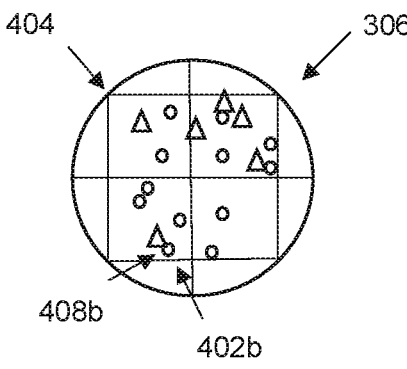
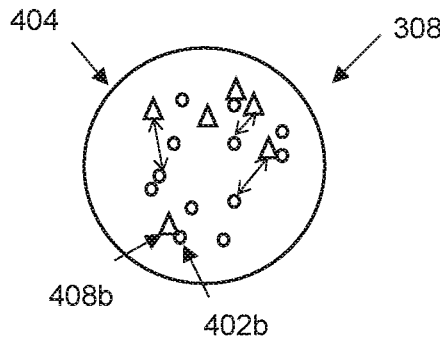
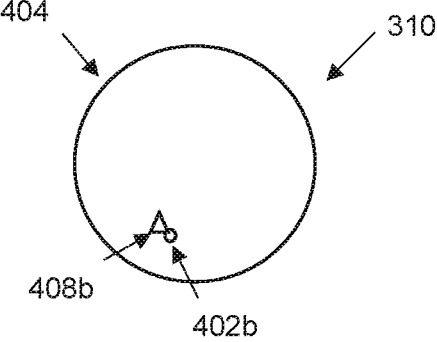
FIG. 4B 312
400
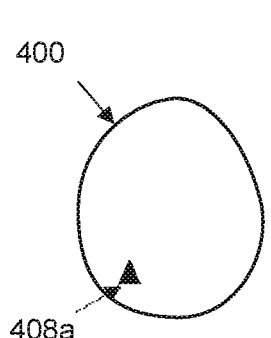
408a
406
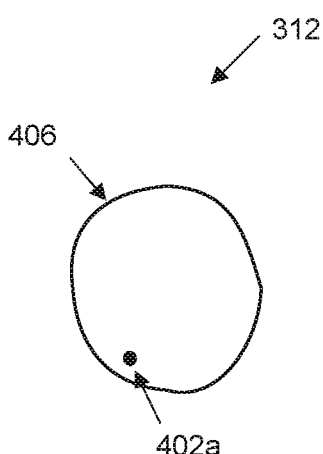
402a
FIG. 4C

600

602
Generate cortical profiles for at least one reference subject and at least one test subject 604
Estimate the value of at least one parameter for at least one reference subject and at least one test subject 606
Determine an estimate of at least one parameter value along the cortical profiles for at least one reference subject and at least one test subject

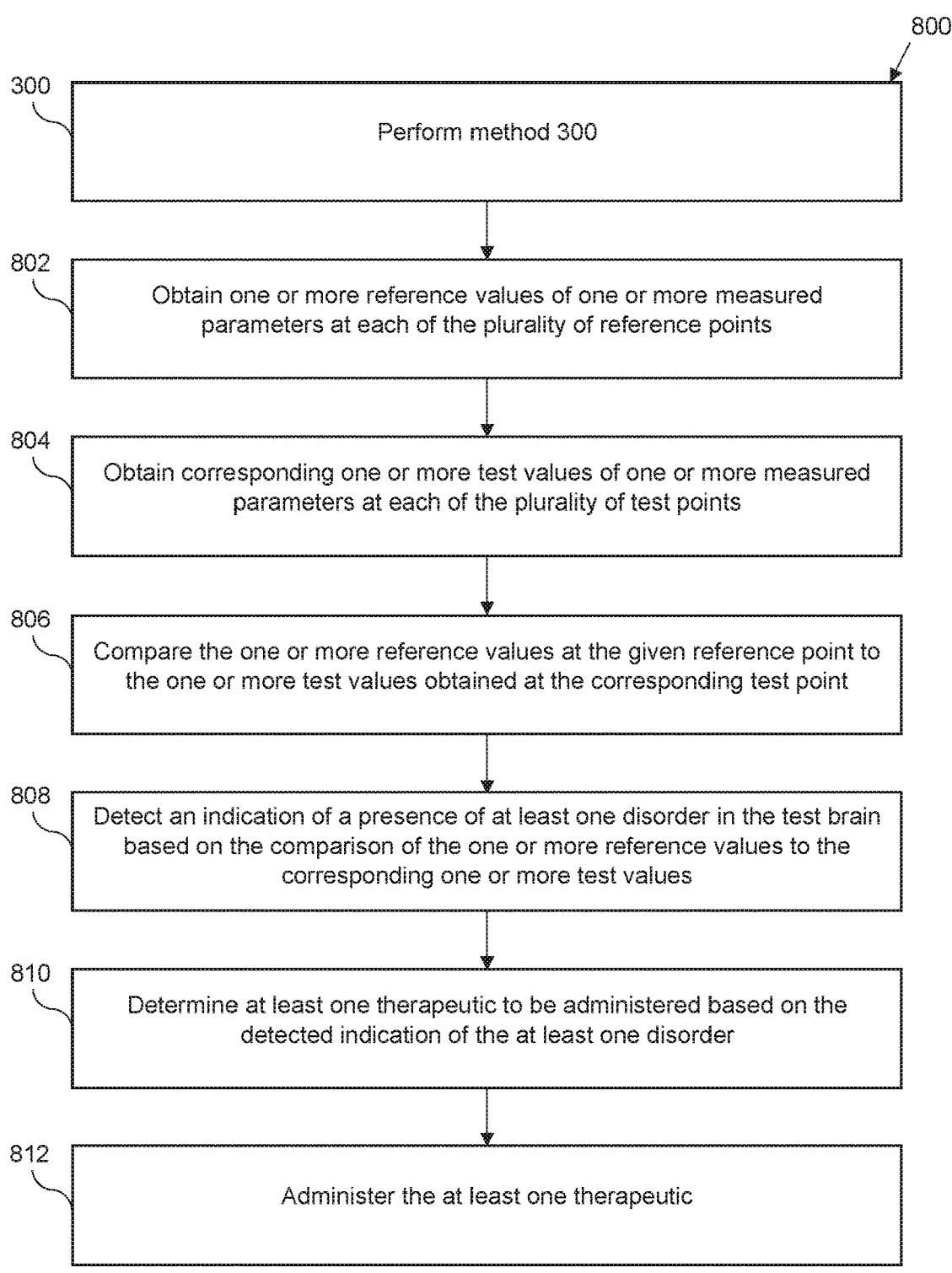

800

300

Perform method 300

802

Obtain one or more reference values of one or more measured parameters at each of the plurality of reference points

804

Obtain corresponding one or more test values of one or more measured parameters at each of the plurality of test points

806

Compare the one or more reference values at the given reference point to the one or more test values obtained at the corresponding test point

808

Detect an indication of a presence of at least one disorder in the test brain based on the comparison of the one or more reference values to the corresponding one or more test values

810

Determine at least one therapeutic to be administered based on the detected indication of the at least one disorder

812

Administer the at least one therapeutic

FIG. 8

BRAIN IMAGE PROCESSING

FIELD OF THE INVENTION

The present technology relates to systems, methods, computer program products, and computer readable media for processing images of brains. In particular, the technology relates to systems, methods, computer program products and computer readable media for processing images of a plurality of brains in order to determine corresponding locations or sample points in the plurality of brains.

BACKGROUND

Brain imaging techniques have evolved rapidly in recent decades, advancing our understanding of brain structure and function. Despite this, comparative studies of human brains are currently very challenging owing to the complexity and diversity and the unique nature of human brains. As a consequence, the ability to perform direct comparisons of multiple brains, and/or specific regions of interest within multiple brains, is limited. It would therefore be beneficial to provide an accurate, consistent, and stable means to allow for the direct comparison of a plurality of brains.

Common neuroimaging techniques include computed tomography (CT), positron emission tomography (PET) and magnetic resonance imaging (MRI). In brief, CT neuroimaging involves reconstructing images from measurements of a series of x-rays applied to the brain volume whilst PET neuroimaging involves reconstructing images from measurements obtained from positron-emitting radiotracers. In contrast, MRI is an imaging technique in which the application of magnetic fields allows arbitrary images of a body, or parts thereof, to be obtained.

In more detail, conventional MRI techniques apply an external static magnetic field ($B_0$) which, when a subject is placed within this field, causes the protons in the body to align with that field. A pulsed radiofrequency field ($B_1$) excites the protons, shifting the protons out of alignment with $B_0$. This shift out of alignment produces a detectable magnetic field which can be used to produce an image.

SUMMARY

Examples or preferred aspects and embodiments of the present technology are set out in the accompanying independent and dependent claims.

This Summary is intended to introduce a selection of concepts in a simplified form that are further described below in the Detailed Description. This Summary is not intended to identify key features or essential features of the claimed subject-matter, nor is it intended to be used to limit the scope of the claimed subject-matter.

According to a first aspect of the present technology, there is provided a method for or of determining correspondence between sample points in brains in a plurality of sets of brain data. The method comprises transforming, into a common space, a plurality of reference points obtained from at least one image of a reference brain in a first space; transforming, into the common space, a plurality of test points obtained from at least one image of a test brain in a second space; determining a position of each of the transformed reference points and each of the transformed test points in the common space; calculating a displacement of each of the transformed test points relative to each of the transformed reference points based on the determined positions; determining a correspondence between one of the transformed test points and a given transformed reference point based on the calculated displacements; and determining a corresponding test point in the second space to a given reference point in the first space based on the determined correspondence. In this way, a consistent number of samples and positions of the samples across a plurality of sets of brain data can be accurately obtained.

In some embodiments, the determining of the correspondence between one of the transformed test points and the given transformed reference point comprises determining the transformed test point having a minimum displacement relative to the given transformed reference point. In this way, the transformed test point having the smallest displacement relative to the transformed reference point is able to be accurately identified.

In some embodiments, the determining of the position in the common space of each of the transformed reference and test points comprises determining respective sets of reference coordinates and test coordinates for the transformed reference points and test points. In this way, an accurate correspondence between the transformed test point and transformed reference point is able to be determined.

In some embodiments, the calculating of the displacement of each of the transformed test points relative to each of the transformed reference points comprises calculating an offset between each set of test coordinates and each set of reference coordinates. In this way, a relative offset between the sets of coordinates is calculable in order to provide an accurate estimate of the displacement between the test points and the reference points.

In some embodiments, the determining of the correspondence between one of the transformed test points and the given transformed reference point comprises determining the set of test coordinates having a minimum offset relative to the set of reference coordinates of the given transformed reference point. In this way, the transformed test point having the smallest displacement relative to the transformed reference point is able to be accurately identified.

In some embodiments, the set of reference coordinates and the set of test coordinates comprise at least one of Cartesian coordinates or radial coordinates.

In some embodiments, the method comprises obtaining one or more reference values of one or more measured parameters at each of the plurality of reference points; and obtaining corresponding one or more test values of one or more measured parameters at each of the plurality of test points. In this way, estimates of parameter values are obtained at each of the reference points and each of the test points.

In some embodiments, the method comprises comparing the one or more reference values at the given reference point to the one or more test values obtained at the corresponding test point. In this way, the measurement of parameters across subjects is more stable. Recall that the method enables a much higher degree of comparability between individual samples across subjects; as a consequence, establishment of the correspondence between points allows for more consistent measuring of the parameters at these sample points.

In some embodiments, the one or more measured parameters comprises at least one of a principal diffusion component-based parameter, a minicolumn-based parameter, or a diffusion-based parameter. In this way, an estimate of at least one of a principal diffusion component-based parameter, a minicolumn-based parameter or a diffusion-based parameter can be obtained, allowing comparability of such parameters across subjects.

In some embodiments, the principal diffusion component-based parameter comprises at least one of an angle of deviation between the principal diffusion direction and a columnar direction of a vertical column through the cortical layer of the brain, perpendicular diffusivity or parallel diffusivity, the minicolumn-based parameter comprises at least one of a minicolumn width, a minicolumn spacing, an axonal fibre bundle width, an axonal fibre bundle spacing, a dendritic fibre bundle width, a dendritic fibre bundle spacing, a minicolumn core width, or minicolumn peripheral neuropil space, and the diffusion-based parameter comprises at least one of mean minicolumn diffusivity, radial diffusivity, fractional anisotropy, mean diffusivity or axial diffusivity. In this way, an estimate of at least one of the aforementioned parameters is obtained, allowing comparability of such parameters across subjects.

In some embodiments, the method comprises obtaining an indication of a prognosis of at least one disorder in the test brain based on the comparison of the one or more reference values at the given reference point to the one or more test values obtained at the corresponding test point. In this way, the direct comparability of estimates of parameters across subjects enables a prognosis of the at least one disorder identifiable in the test brain to be determined. A test subject and/or clinical staff are able to make educated decisions on subsequent treatment and care based on the indication of the prognosis of at least one brain disorder.

In some embodiments, the method comprises detecting an indication of a presence of at least one disorder in the test brain based on the comparison of the one or more reference values at the given reference point to the one or more test values obtained at the corresponding test point. In this way, a test subject and/or clinical staff are able to make educated decisions on subsequent treatment and care based on the detected indication of the presence of at least one brain disorder.

In some embodiments, the at least one disorder comprises a neurodegenerative disorder, a neuroinflammatory disorder, a neurodevelopmental disorder, a psychiatric disorder, or a brain disorder associated with a SARS-CoV-2 infection.

In some embodiments, the at least one disorder comprises Alzheimer's Disease, cerebrovascular dementia, mild cognitive impairment, frontotemporal dementia, dementia with Lewy Bodies, autism, an autism spectrum disorder, multiple sclerosis, epilepsy, amyotrophic lateral sclerosis, Parkinson's disease, schizophrenia, bipolar disorder, dyslexia, Down's syndrome, Huntington's disease, prion disease, depression, obsessive-compulsive disorder, attention deficit hyperactivity disorder, or chronic traumatic encephalopathy.

In some embodiments, the method comprises detecting an indication of at least one injury in the test brain based on the comparison of the one or more reference values at the given reference point to the one or more test values obtained at the corresponding test point. In this way, a test subject and/or clinical staff are able to make educated decisions on subsequent treatment and care based on the detected indication of at least one injury in the test brain.

In some embodiments, the at least one injury comprises a mild traumatic brain injury, a concussion, a cerebral contusion, an anoxic brain injury, or a hypoxic brain injury.

In some embodiments, the method comprises determining a measure of brain health in the test brain based on the comparison of the one or more reference values at the given reference point to the one or more test values obtained at the corresponding test point. In this way, a test subject and/or clinical staff are able to make educated decisions on subsequent treatment, care, and/or lifestyle based on the determined measure of brain health.

In some embodiments, the method comprises determining at least one therapeutic to be administered based on the detected indication of the prognosis of at least one disorder in the test brain, the presence of at least one disorder in the test brain, the detected indication of at least one injury in the test brain and/or the determined measure of brain health in the test brain. In this way, the test subject is able to receive more suitable treatment based on the determination of the at least one therapeutic to be administered.

In some embodiments, the method comprises determining at least one non-pharmacological treatment to be implemented based on the detected indication of the prognosis of at least one disorder in the test brain, the detected indication of the presence of at least one disorder in the test brain, the detected indication of at least one injury in the test brain and/or the determined measure of brain health in the test brain. In this way, the test subject is able to receive more suitable treatment and/or adopt beneficial changes based on the determination of the at least one therapeutic to be administered.

In some embodiments, the at least one image of the reference brain comprises at least one of a brain atlas, an image of a control brain or a second image of the test brain, wherein the control brain comprises a different brain to the test brain.

In some embodiments, the common space is a substantially spherical space. In this way, the common space can act as an abstract representation of a brain.

In some embodiments, the reference points and the test points comprise grey matter surface vertices.

In some embodiments, each of the plurality of reference points is representative of a known marker in the reference brain, and each of the plurality of test points is representative of a known marker in the test brain. In this way, the same known marker in each reference brain and in each test brain can be identified.

According to a second aspect of the present technology, there is provided a system for determining correspondence between sample points in brains in a plurality of sets of brain data. The system comprises at least one processor and memory storing computer-executable instructions that, when executed by the one or more processors, cause the at least one processor to transform, into a common space, a plurality of reference points obtained from at least one image of a reference brain in a first space; transform, into the common space, a plurality of test points obtained from at least one image of a test brain in a second space; determine a position of each of the transformed reference points and each of the transformed test points in the common space; calculate a displacement of each of the transformed test points relative to each of the transformed reference points based on the determined positions; determine a correspondence between one of the transformed test points and a given transformed reference point based on the calculated displacements; and determine a corresponding test point in the second space to a given reference point in the first space based on the determined correspondence. In this way, a consistent number of samples and positions of the samples across a plurality of sets of brain data can be accurately obtained using the system.

According to a third aspect of the present technology, there is provided a computer program product comprising instructions which, when the program is executed by a computer, cause the computer to transform, into a common space, a plurality of reference points obtained from at least one image of a reference brain in a first space; transform, into the common space, a plurality of test points obtained from at least one image of a test brain in a second space; determine a position of each of the transformed reference points and each of the transformed test points in the common space; calculate a displacement of each of the transformed test points relative to each of the transformed reference points based on the determined positions; determine a correspondence between one of the transformed test points and a given transformed reference point based on the calculated displacements; and determine a corresponding test point in the second space to a given reference point in the first space based on the determined correspondence. In this way, a consistent number of samples and positions of the samples across a plurality of sets of brain data can be accurately obtained using the computer program product.

According to a fourth aspect of the present technology, there is provided a computer-readable medium comprising instructions which, when executed by a computer, cause the computer to transform, into a common space, a plurality of reference points obtained from at least one image of a reference brain in a first space; transform, into the common space, a plurality of test points obtained from at least one image of a test brain in a second space; determine a position of each of the transformed reference points and each of the transformed test points in the common space; calculate a displacement of each of the transformed test points relative to each of the transformed reference points based on the determined positions; determine a correspondence between one of the transformed test points and a given transformed reference point based on the calculated displacements; and determine a corresponding test point in the second space to a given reference point in the first space based on the determined correspondence. In this way, a consistent number of samples and positions of the samples across a plurality of sets of brain data can be accurately obtained using the computer-readable medium.

According to a fifth aspect of the present technology, there is provided a method of treatment for treating a brain disorder. The method comprises transforming, into a common space, a plurality of reference points obtained from at least one image of a reference brain in a first space; transforming, into the common space, a plurality of test points obtained from at least one image of a test brain in a second space; determining a position of each of the transformed reference points and each of the transformed test points in the common space; calculating a displacement of each of the transformed test points relative to each of the transformed reference points based on the determined positions; determining a correspondence between one of the transformed test points and a given transformed reference point based on the calculated displacements; determining a corresponding test point in the second space to a given reference point in the first space based on the determined correspondence; obtaining one or more reference values of one or more measured parameters at each of the plurality of reference points; obtaining corresponding one or more test values of one or more measured parameters at each of the plurality of test points; comparing the one or more reference values at the given reference point to the one or more test values obtained at the corresponding test point; detecting an indication of a presence of at least one disorder in the test brain based on the comparison of the one or more reference values at the given reference point to the one or more test values obtained at the corresponding test point; determining at least one therapeutic to be administered based on the detected indication of the prognosis of at least one disorder in the test brain, the presence of at least one disorder in the test brain, the detected indication of at least one injury in the test brain and/or the determined measure of brain health in the test brain; and administering said at least one therapeutic. In this way, treatments are administrable based on the detected indication of a deviation in the test brain.

In some embodiments, the at least one therapeutic comprises a small molecule drug, a biologic, or a polynucleotide delivered by a vector or a particle.

In some embodiments, the at least one disorder comprises Alzheimer's disease and the at least one therapeutic comprises a cholinesterase inhibitor, an N-methyl-D-aspartate antagonist, or a monoclonal antibody, or wherein the at least one disorder comprises Parkinson's disease and the at least one therapeutic comprises a central nervous system agent, a decarboxylase inhibitor, a dopamine agonist, a monoamine oxidase-B inhibitor, a catechol-O-methyltransferase inhibitor, or an adamantane. In this way, specifically targeted treatments can be adopted.

According to a sixth aspect of the present technology, there is provided a method of treatment. The method of treatment comprises transforming, into a common space, a plurality of reference points obtained from at least one image of a reference brain in a first space; transforming, into the common space, a plurality of test points obtained from at least one image of a test brain in a second space; determining a position of each of the transformed reference points and each of the transformed test points in the common space; calculating a displacement of each of the transformed test points relative to each of the transformed reference points based on the determined positions; determining a correspondence between one of the transformed test points and a given transformed reference point based on the calculated displacements; determining a corresponding test point in the second space to a given reference point in the first space based on the determined correspondence; obtaining one or more reference values of one or more measured parameters at each of the plurality of reference points; obtaining corresponding one or more test values of one or more measured parameters at each of the plurality of test points; comparing the one or more reference values at the given reference point to the one or more test values obtained at the corresponding test point; detecting an indication of a presence of at least one disorder in the test brain based on the comparison of the one or more reference values at the given reference point to the one or more test values obtained at the corresponding test point; determining at least one non-pharmacological treatment to be implemented based on the detected indication of the prognosis of at least one disorder in the test brain, the detected indication of the presence of at least one disorder in the test brain, the detected indication of at least one injury in the test brain and/or the determined measure of brain health in the test brain; and implementing said at least one non-pharmacological treatment. In this way, alternative treatments based on the detected indication of a deviation in the test brain are able to be implemented.

In some embodiments, the at least one disorder comprises Alzheimer's disease and the at least one non-pharmacological treatment comprises cognitive stimulation therapy, cognitive rehabilitation, or cognitive behavioural therapy, or wherein the at least one disorder comprises Parkinson's disease and the at least one non-pharmacological treatments comprises physiotherapy, speech and language therapy, deep brain stimulation, or occupational therapy. In this way, the most suitable treatments can be adopted.

According to a seventh aspect of the present technology, there is provided a computer-implemented method. The method comprises transforming, into a common space, a plurality of reference points obtained from at least one image of a reference brain in a first space, wherein each of the reference points are associated with a relative reference position in the first space; transforming, into the common space, a plurality of test points obtained from at least one image of a test brain in a second space, wherein each of the test points are associated with a relative test position in the second space; determining a position of each of the transformed reference points and each of the transformed test points in the common space; calculating a displacement of each of the transformed test points relative to each of the transformed reference points based on the determined positions; determining a correspondence between one of the transformed test points and a given transformed reference point based on the calculated displacements; determining a corresponding test point in the second space to a given reference point in the first space based on the determined correspondence, wherein the relative test position and the relative reference position are substantially equivalent points in the test brain and the reference brain; obtaining one or more reference values of one or more measured parameters at each of the plurality of reference points; obtaining corresponding one or more test values of one or more measured parameters at each of the plurality of test points; comparing the one or more reference values at the given reference point to the one or more test values obtained at the corresponding test point; and obtaining an indication of a prognosis of at least one disorder in the test brain and/or an indication of a presence of at least one disorder in the test brain based on the comparison of the one or more reference values at the given reference point to the one or more test values obtained at the corresponding test point. In this way, a consistent number of samples and positions of the samples across a plurality of sets of brain data can be accurately obtained, allowing inferences regarding at least one deviation in the test brain to be made.

It will be apparent to anyone of ordinary skill in the art, that some of the features indicated above as preferable in the context of one of the aspects of the present technology may replace one or more of the preferred features of other preferred features of the present technology. Such apparent combinations are not explicitly listed above under each such possible additional aspect for the sake of conciseness.

Other examples will become apparent for the following detailed description, which, when taken in conjunction with the drawings, illustrate by way of example the principles of the present technology.

BRIEF DESCRIPTION OF THE DRAWINGS

The accompanying drawings illustrate various examples of the present technology. Common reference numerals are used throughout the figures, where appropriate, to indicate similar features.

FIG. 1 illustrates a simplified method for performing cortical reconstruction and volumetric segmentation of the acquired structural MRI data.

FIG. 2 illustrates a simplified method for processing diffusion-weighted images.

FIG. 3 illustrates an exemplary method for determining correspondence between sample points in brains in a plurality of sets of brain data.

FIG. 4B illustrates a simplified abstract representation of a method for determining a correspondence between a transformed test point and a given reference point in the common space.

FIG. 4C illustrates a simplified abstract representation of a method for determining a correspondence between an untransformed test point in a second space and a given untransformed reference point in a first space.

FIG. 8 illustrates an exemplary method of treatment according to aspects of the present invention.

Figure 4A:
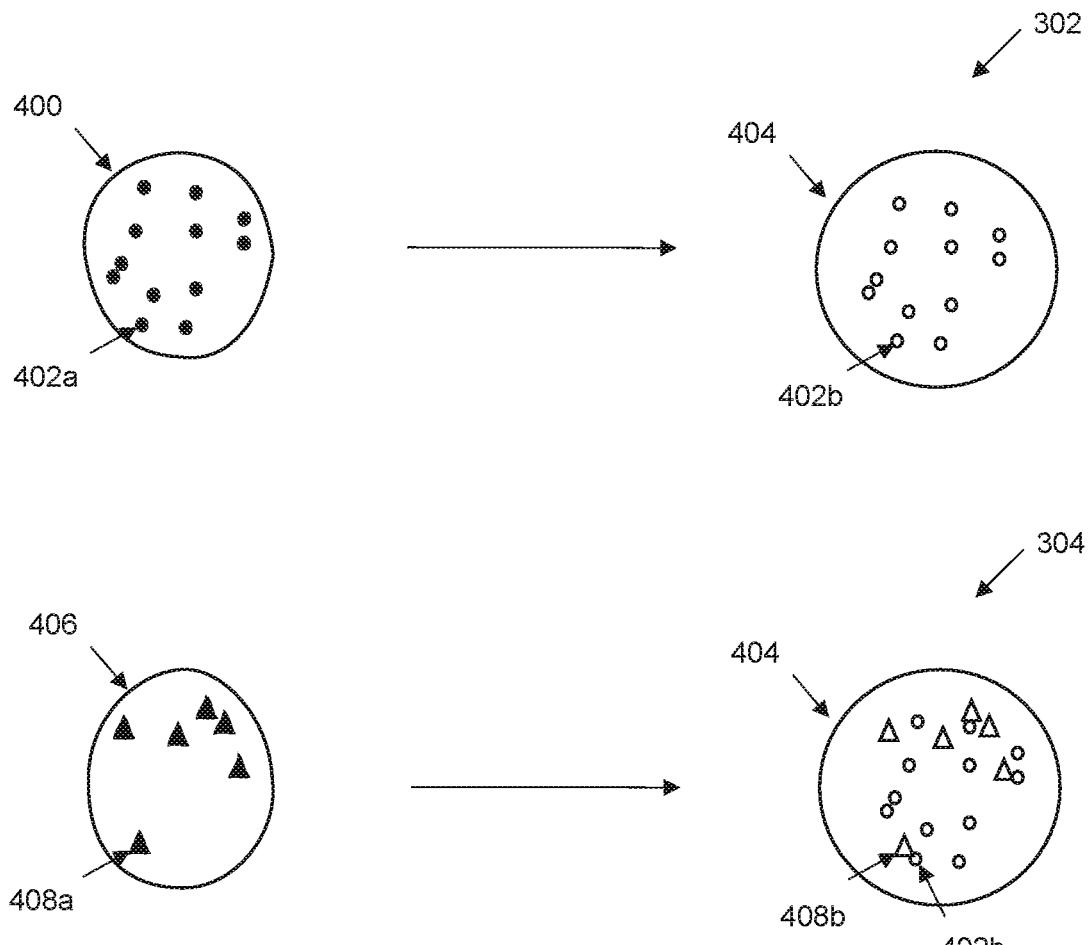
FIG. 4A illustrates a simplified abstract representation of a method for transforming reference points and test points into a common space.

The accompanying drawings illustrate various examples. Common reference numerals are used throughout the figures, where appropriate, to indicate similar features.

DETAILED DESCRIPTION

The following description is made for the purpose of illustrating the general principles of the present technology and not intended to limit the inventive concepts as outlined herein. The following description is presented by way of example to enable a person skilled in the art to make and use the present technology. The present technology is not limited to the embodiments described herein and various modifications to the disclosed embodiments will be readily apparent to anyone skilled in the art.

The present technology relates to systems, methods, computer program products, and computer readable media for processing images of brains. In particular, the technology relates to systems, methods, computer program products and computer readable media for processing images of a plurality of brains in order to determine corresponding locations or sample points in the plurality of brains.

Magnetic resonance imaging is playing an increasingly valuable role in advancements made in the field of neuroscience. However, as conventional magnetic resonance (MR) images are expressed in arbitrary units, intensities in MR images vary across sites, subjects, and time points. As such, it is difficult to perform accurate direct comparisons on conventional MR images (Fortin, J. P. et al. (2016). 'Removing inter-subject technical variability in magnetic resonance imaging studies'. Neuroimage. 132, pp 198-212).

Conventional MRI techniques may include the acquisition of T1- and T2-weighted images. The contrast and brightness of T1- and T2-weighted images are primarily influenced by the respective T1 and T2 relaxation times of tissue. However, the signal intensities in T1- and T2-weighted images are also dependent on other tissue characteristics and inhomogeneities present in the magnetic field, along with other extraneous factors. As a consequence, the comparability of such images across subjects or time points is limited. Further, traditional techniques for performing image registration of a plurality of brain images are computationally expensive, challenging to use and prone to error. As such, it would be desirable to provide for a means to allow more accurate comparisons of a plurality of brains across subjects or time points to be made. In particular, it would be desirable to be able to identify corresponding locations or sample points in brains across subjects or time points. This would allow parameters or measurements derived from the locations or sample points to be more accurately compared. This could enable patients, subjects and/or clinical staff to make better informed decisions on medical treatment and care and could further advance our knowledge and understanding of the complexity and diversity of the brain.

Additionally, variability in scanner hardware, subject motion, image noise, and processing techniques can affect the repeatability of MRI scanning in traditional longitudinal studies in which the same subject is scanned on the same scanner at multiple different time points (Borga, M. et al. (2020) 'Reproducibility and repeatability of MRI-based body composition analysis.' Magnetic Resonance in Medicine. 84, pp. 3146-3156).

Moreover, the reproducibility of methods in studies where subjects are scanned on multiple different scanners at multiple different time points is also affected by the usage of different scanners, resulting in different implementations of the pulse sequences. Further variability in cross-sectional studies arises owing to differences in processing techniques, variance in hardware setup and characteristics, and subject motion (Borga, M. et al. (2020) 'Reproducibility and repeatability of MRI-based body composition analysis.' Magnetic Resonance in Medicine. 84, pp. 3146-3156). Variability may also be introduced into multi-site studies owing to routine maintenance of scanners. This is further confounded by the tendency of different sites and different operators to use different MRI sequences.

Variability between- and across-sites may also arise due to dependence on environmental factors. In turn, this can affect the reproducibility and comparability of the MR imaging techniques used at these sites. In addition, when acquiring and processing data, researchers may use a mixture of pipelines and/or in-house tools, which can introduce additional variability. Studies have also shown that the reproducibility and comparability of processed images are affected by the usage of different workstations to process brain images (Gronenschild, E. H. et al. (2012). 'The Effects of FreeSurfer Version, Workstation Type, and Macintosh Operating System Version on Anatomical Volume and Cortical Thickness Measurements.' PLOS One. 7(6), e38234).

Further variability may arise owing to the acquisition protocol employed. For example, as noted previously, whilst the image contrast in T1-weighted and T2-weighted images is primarily influenced by T1 and T2 relaxation times respectively, the effects of other factors such as proton density and relative relaxation rates are also noticeable in the resultant images. Further, diffusion measures have been shown to be influenced by a range of different factors including variance in acquisition techniques, processing techniques, b-value, signal-to-noise ratio, the resolution of the images, scanner hardware, co-registration of images and reslicing, thereby affecting the suitability of diffusion-weighted images for comparative studies (Bisdas, S. et al. (2008) 'Reproducibility, interrater agreement, and age-related changes of fractional anisotropy measures at 3T in healthy subjects: Effect of the applied b-value.' American Journal of Neuroradiology. 29 (6), pp. 1128-1133; Correia, M. M. et al. (2009) 'Looking for the optimal DTI acquisition scheme given a maximum scan time: Are more b-values a waste of time?' Magnetic Resonance Imaging. 27 (2), pp. 163-175; Papinutto, N. D. et al. (2013) 'Reproducibility and biases in high field brain diffusion MRI: An evaluation of acquisition and analysis variables.' Magnetic Resonance Imaging. 31 (6), pp. 827-839; Takao, H. et al. (2012) 'Effect of scanner in longitudinal diffusion tensor imaging studies.' Human Brain Mapping. 33(2), pp. 466-477. Zhu, T. et al. 'Quantification of accuracy and precision of multi-center DTI measurements: A diffusion phantom and human brain study.' Neuroimage. 56(3), pp. 1398-1411).

In a typical MRI processing pipeline, volumes may undergo segmentation and parcellation to derive regions of interest (ROIs). Measures such as surface area, white matter volume, grey matter volume and cortical thickness for each ROI may be computed. Further, with regard to diffusion-weighted images, provided appropriate registration methods are employed, estimates of diffusion parameters within suitable ROIs may be derived. Spatial normalisation of such images may allow group analyses to be performed. Spatial normalisation essentially resamples the relevant structural or diffusion data of each subject into the same coordinate space. This may be achieved by registering all of the brains within a cohort to each other, or by normalising each of the brains to a standardised template. Further statistical analyses may then be performed in order to compare the resampled data and the derived estimates. This method of normalisation, however, does not allow for the exact anatomical correspondence of sampling points in brains to be determined across subjects.

Owing to differences in human brain shape and size, it is very challenging to define exact anatomical correspondence in different brains, or in the same brain over time. In turn, the ability to perform accurate and reliable direct comparisons of brain data, and estimates derived therefrom, is currently not possible. As such, there is a need to provide methods and systems for processing brain images to allow for more accurate and reliable comparisons to be made across subjects and time points, thereby enabling more consistent estimates of parameters to be acquired.

The present technology relates to systems, methods, computer program products, and computer readable media for processing images of brains. In particular, the technology relates to systems, methods, computer program products and computer readable media for processing images of a plurality of brains in order to determine corresponding locations or sample points in the plurality of brains.

In the present technology, at least one structural MR image is obtained for each subject, along with diffusion-weighted MR images for each subject. In an example, image data may be acquired at a single time point. Alternatively, image data may be acquired at a plurality of time points on the same scanner. In a further alternative example, image data may be acquired at a plurality of time points on different scanners. In a still further alternative example, images may be acquired at three or more time points on a mixture of the same or different scanners. Images may be acquired on MRI scanners of suitable strength for imaging and the scanners may be of any manufacturer.

The at least one structural MR image and diffusion-weighted MR images are acquired from at least one reference subject and at least one test subject.

The at least one reference subject may be any human individual. The at least one reference subject may be healthy, in which the at least one reference subject is considered to not have any brain disorders. The at least one reference subject may be non-healthy, in which the at least one reference subject is considered to have a brain disorder or an indication of a least one abnormality in the brain. In an example, the at least one reference brain may be derived from a plurality of reference brains; in this example, the plurality of reference brains may all be healthy, or non-healthy, or a mixture of healthy and non-healthy. The one of ordinary skill in the art appreciates that the reference brain may be any suitable control brain or derived from a plurality of suitable control reference brains. Furthermore, whilst the systems, methods, computer program products and computer readable media as described herein are outlined with respect to a human reference subject, the one of ordinary skill in the art appreciates that the at least one reference subject may be any other suitable mammalian reference subject.

The at least one test subject may be any human individual. The at least one test subject may be healthy, in which the at least one test subject is considered to not have any brain disorders. The at least one test subject may be non-healthy, in which the at least one test subject is considered to have a brain disorder or an indication of a least one abnormality in the brain. In an example, the at least one test brain may be derived from a plurality of test brains; in this example, the plurality of test brains may all be healthy, or non-healthy, or a mixture of healthy and non-healthy. Whilst the systems, methods, computer program products and computer readable media as described herein are outlined with respect to a human test subject, the one of ordinary skill in the art appreciates that the at least one test subject may be any other suitable mammalian test subject.

In an example, the at least one structural image may comprise high-resolution T1-weighted 3D MP-RAGE images (TR/TE-2040/4.7 ms, resolution=1×1×1 mm³, FOV=192×192 mm²).

In an alternative example, the at least one structural image may comprise high-resolution T1-weighted 3D MDEFT images (TR/TE=1338/2.4 ms, resolution=resolution=1×1×1 mm³, FOV=250×250 mm²).

In a further alternative example, the at least one structural image may comprise Accelerated Sagittal MPRAGE images (TR/TE=2300/2.95 ms, resolution=1×1×1 mm³, FOV=209× 240×256 mm²).

In an example, the diffusion-weighted imaging data may comprise diffusion-weighted images acquired using a spin-echo echo planar imaging (SE-EPI) sequence (TR/TE=9300/94 ms; isotropic resolution=2.2 mm³, flip angle=90°, b factor=1000 s/mm²), with 60 images with diffusion gradients applied in 60 non-collinear directions and two b0 images.

In an alternative example, the diffusion-weighted imaging data may comprise diffusion-weighted images acquired using a twice-refocused SE-EPI sequence (TR/TE=10200/85 ms, isotropic resolution=2.3 mm³, flip angle=90°, b factor=1000 s/mm²), with 61 images with diffusion gradients applied in 61 non-collinear directions and seven b0 images.

In a further example, the diffusion-weighted imaging data may comprise diffusion-weighted images of the following acquisition (TR/TE=7200/56 ms, isotropic resolution=2.0 mm³, flip angle 90°, b factor=1000 s/mm²), with 54 images with diffusion gradients applied in 54 non-collinear directions and one b0 image.

It is appreciated by one of ordinary skill in the art that any suitable acquisition protocols may be used to acquire the respective diffusion-weighted data and the structural data.

In an embodiment, the data are acquired using the same diffusion-weighted acquisition protocol and the same structural acquisition protocol for each subject. In other embodiments, the diffusion data and/or the structural data may be acquired for each subject using different acquisitions.

At least one structural MR image is acquired for each reference subject and for each test subject. In an example, the structural image may be at least one of a T1-weighted image, a T2-weighted image, a FLAIR image, or a magnetisation transfer image. The T1-weighted image may be acquired according to the examples described previously and the one of ordinary skill in the art appreciates that the at least one T1-weighted image may be acquired using any acquisition parameters suitable for deriving T1-weighted images. The one of ordinary skill in the art appreciates that, in examples where the at least one structural image comprises a T2-weighted image, a FLAIR image, or a magnetisation transfer image, that these respective images may be acquired using any acquisition parameters suitable for deriving such images.

In an example, a plurality of structural images may be acquired for each subject. The plurality of images may be acquired in the same acquisition or may be acquired in different acquisitions.

FIG. 1 depicts a simplified method 100 for performing cortical reconstruction and volumetric segmentation of the acquired structural MRI data. In this example, the structural MRI data comprises at least one T1-weighted image. In other examples, the one of ordinary skill in the art appreciates that alternative or additional techniques may be used to process the acquired structural MRI data, wherein the structural MRI data may comprise at least one of a T2-weighted image, a FLAIR image, or a magnetisation transfer image.

At block 102, the at least one structural magnetic resonance image acquired for at least one reference subject and at least one test subject is received. In this example, the structural MRI data comprises at least one T1-weighted image.

Optionally, in an example where a plurality of structural images are acquired for the at least one reference subject and the at least one test subject, the plurality of images for each given subject may be spatially registered and a single, motion corrected averaged output of the scans may be generated.

At block 104, for each original volume received, a transformation matrix to a standard atlas is computed. In an example, for each original volume, an affine transform to the MNI305 atlas may be computed. Optionally, the computation of the transform may be checked and manually corrected.

At block 106, non-uniform intensity correction and intensity normalisation is performed for each set of MR data received. This allows for the removal of intensity non-uniformity in the MR data. Further, intensities for all voxels are scaled to correct for fluctuations in intensity and an intensity corrected structural volume is generated for each of the original volumes received.

At block 108, each intensity-corrected structural volume is skull-stripped and corrected for noise and a brain mask is generated.

At block 110, segmentation of the subcortical white matter and deep grey matter is performed. In an example, the subcortical segmentation may include performing an initial registration to a template, performing a normalisation based on a model of the atlas, computing a nonlinear transform to align with the template, removal of the neck of the subject, and computing a transform to align the no-neck volume with the template volume including the skull. Volumetric labelling is performed by assigning each voxel in the normalized brain volume a label. The labels include cerebral white matter, cerebral cortex, lateral ventricle, inferior lateral ventricle, cerebellum white matter, cerebellum cortex, thalamus, caudate, putamen, *pallidum*, hippocampus, amygdala, lesion, accumbens area, vessel, third ventricle, fourth ventricle, brain stem, and cerebrospinal fluid. At least one segmentation volume is output. Statistics for the segmented subcortical structures may be computed. White matter segmentation is performed using the skull-stripped brain volume that has undergone further intensity normalization.

At block 112, cortical and white matter surfaces and curvature outputs for cortical thickness are created. An original surface is created, smoothed, and inflated before topology fixing is performed. The white matter surface is generated by deforming the original surface by following the white-grey intensity gradient in the T1 volume. The cortical surface is created by expanding the white matter surface by following the grey matter-cerebral spinal fluid intensity gradient in the T1 volume. Binary volume masks of the cortical ribbon are generated.

At block 114, spherical morphing is performed. The original surface is registered to a spherical atlas based on individual cortical folding patterns. Both ipsilateral and contralateral spherical atlases may be used. The average curvature from the spherical atlas is resampled to the curvature of the subject.

At block 116, cortical parcellation is performed. A neuroanatomical label is assigned to each cortical surface vertex. Cortical parcellation statistics for each structure may be output.

The outputs from the reconstruction process may include estimates of the cortical grey matter (GM) volume, the white matter (WM) volume, the cortical surfaces, and the cortical thickness. Further outputs may include WM hyperintensity volumes. Additionally, hippocampal volumes may be derived and averaged to yield an estimate of the bilateral hippocampal volume. Volumes may be expressed as a percentage of the total intracranial volume.

Optionally, the grey matter mask may be eroded to reduce for any partial volume effect. In an example, the erosion may be by 0.5 mm, 1 mm or by 1.5 mm.

Optionally, any of the outputs at any of the stages of the reconstruction process may be visually inspected. If any errors are detected, the erroneous data set may be re-run through the pipeline. In some examples, the data set may be excluded from the subsequent analyses. In some examples, errors in the outputs may be corrected manually.

In an example, a tool such as Freesurfer (http://surfer.nmr.mgh.harvard.edu) may be used to perform the structural processing. Technical details of the reconstruction process of Freesurfer are found in various prior publications (Dale, A. M. & Sereno, M. I. (1993). 'Improved localization of cortical activity by combining EEG and MEG with MRI cortical surface reconstruction: a linear approach'. Journal of Cognitive Neuroscience. 5, pp. 162-176; Dale, A. M. et al. (1999). 'Cortical surface-based analysis. I. Segmentation and surface reconstruction.' Neuroimage. 9, pp. 179-194; Fischl, B. et al. (1999). 'Cortical surface-based analysis. II: Inflation, flattening, and a surface-based coordinate system'. Neuroimage. 9, pp. 195-207; Fischl, B. (1999). 'High-resolution intersubject averaging and a coordinate system for the cortical surface'. Human Brain Mapping. 8, pp. 272-284; Fischl, B. & Dale, A. M. (2000). 'Measuring the thickness of the human cerebral cortex from magnetic resonance images.' Proceedings of the National Academy of Sciences USA. 97, pp. 11050-11055; Fischl, B. et al. (2001). 'Automated manifold surgery: constructing geometrically accurate and topologically correct models of the human cerebral cortex'. IEEE Transactions on Medical Imaging. 20, pp. 70-80; Fischl, B. et al. (2002). 'Whole brain segmentation: automated labeling of neuroanatomical structures in the human brain'. Neuron. 33, pp. 341-355; Fischl, B. et al. (2004). 'Sequence-independent segmentation of magnetic resonance images'. Neuroimage. 23, Supplement 1, S69-84; Fischl, B. et al. (2004). 'Automatically parcellating the human cerebral cortex. Cerebral Cortex. 14, pp. 11-22; Han, X. et al. (2006). 'Reliability of MRI-derived measurements of human cerebral cortical thickness: the effects of field strength, scanner upgrade and manufacturer'. Neuroimage. 32, pp. 180-194; Jovicich, J. et al. (2006). 'Reliability in multi-site structural MRI studies: effects of gradient non-linearity correction on phantom and human data'. Neuroimage. 30, pp. 436-443; Reuter, M. et al. (2010). 'Highly Accurate Inverse Consistent Registration: A Robust Approach.' Neuroimage. 53(4), pp. 1181-1196; Reuter, M. et al. (2012). 'Within-Subject Template Estimation for Unbiased Longitudinal Image Analysis'. Neuroimage. 61(4), pp. 1402-1418; Segonne, F. et al. (2004) 'A hybrid approach to the skull stripping problem in MRI'. Neuroimage. 22, pp. 1060-1075). The one of ordinary skill in the art appreciates that other tools and/or suitable methods may be used in order to perform the reconstruction process.

Diffusion-weighted scans are acquired for the at least one reference subject and the at least one test subject.

FIG. 2 illustrates a simplified method 200 for processing diffusion-weighted images for the at least one reference subject and the at least one test subject.

At block 202, the acquired diffusion-weighted images are received for the at least one reference subject and the at least one test subject. Optionally, the diffusion data may be visually checked to detect indications of artifacts or corrupted volumes for any of the subjects. If any errors are detected, the diffusion data may be excluded from the subsequent analyses.

At block 204, the diffusion-weighted images are corrected for susceptibility-induced distortions and eddy current effects for the at least one reference subject and the at least one test subject. All of the acquired diffusion-weighted images for each subject may be aligned to a reference b0 image. Corrected diffusion-weighted images are generated. In an example, a tool such as FSL may be used to perform the corrections (https://fsl.fmrib.ox.ac.uk/fsl/fsiwiki/FSL Andersson, J. L. R. et al. (2016) 'An integrated approach to correction for off-resonance effects and subject movement in diffusion MR imaging'. Neuroimage. 125, pp. 1063-1078; Graham, M. S. et al. (2017). 'Quantitative assessment of the susceptibility artefact and its interaction with motion in diffusion MRI'. PloS One. 12(10)). In alternative examples, the one of ordinary skill in the art appreciates that any suitable pipeline or method for performing the corrections as described herein may be used.

At block 206, a diffusion tensor model is fitted at each voxel. Typical outputs of the diffusion tensor fitting include maps of mean diffusivity, fractional anisotropy, and mode of anisotropy, along with maps of each of the eigenvectors, and each of the eigenvalues, and a raw T2 signal image with no diffusion weighting. Additional outputs may include maps of the sum of squared error of the fit of the diffusion tensor model. Any of these maps may be referred to as a diffusion map. In an example, a tool such as FSL may be used to perform the diffusion tensor fitting (https://fsl.fmrib.ox-.ac.uk/fsl/fslwiki/FSL). In alternative examples, the one of ordinary skill in the art appreciates that any suitable pipeline or method for fitting of the diffusion tensor model as described herein may be used.

At block 208, the eddy-corrected diffusion-weighted images are registered to the skull-stripped structural image as generated in the reconstruction process. In more detail, the white matter segmentation obtained in the reconstruction process is mapped to the diffusion-weighted image. Sample pairs of the intensity values are determined at a predetermined distance either side of the mapped boundary. A cost function is calculated based on the difference calculated between each corresponding pair of intensity values (Greve, D. N and Fischl, B. (2009) 'Accurate and robust brain image alignment using boundary-based registration'. NeuroImage. 48(1), pp. 63-72). Differences above a predetermined thresh-old level are removed and the cost function is used to register the diffusion image to the skull-stripped structural image. In an example, a tool such as FSL may be used to perform the registration (https://fsl.fmrib.ox.ac.uk/fsl/fslwiki/FSL). In alternative examples, the one of ordinary skill in the art appreciates that any suitable pipeline or method for registering the diffusion images to the structural images as described herein may be used.

Optionally, any of the outputs at any of the stages of the processing of the diffusion-weighted images may be visually inspected. If any errors are detected, the erroneous data set may be re-run through the pipeline. In some examples, the data set may be excluded from the subsequent analyses. In some examples, errors in the outputs may be corrected manually.

FIG. 3 illustrates an exemplary method 300 for determin-ing correspondence between sample points in brains in a plurality of sets of brain data.

At block 302, a plurality of reference points obtained from at least one image of a reference brain in a first space are transformed into a common space.

At block 304, a plurality of test points obtained from at least one image of a test brain in a second space are transformed into the common space.

At block 306, a position of each of the transformed reference points and each of the transformed test points in the common space is determined. In an example, the posi-tion of each of the transformed reference points and each of the transformed test points is determined by determining respective sets of reference coordinates and test coordinates for each of the transformed reference points and transformed test points. The set of reference coordinates and the set of test coordinates may comprise at least one of Cartesian coordinates or radial coordinates.

At block 308, a displacement of each of the transformed reference points relative to each of the transformed test points is calculated based on the determined positions. In an example where respective sets of reference and test coordi-nates are determined, the displacement may be calculated by determining an offset between each set of test coordinates and reference coordinates.

At block 310, a correspondence between one of the transformed test points and a given transformed reference point is determined based on the calculated displacements. In an example, the correspondence between one or the transformed test points and the given transformed reference point is determined by determining which transformed test point has a minimum displacement relative to the given transformed reference point. In an example where respective sets of reference and test coordinates are determined and the offset between the respective sets of reference and test coordinates is determined, the correspondence between the transformed test points and the given transformed reference test point may be determined by determining the set of test coordinates that have a minimum offset to the set of refer-ence coordinates of the given transformed reference point. The minimum offset may be described by the smallest relative offset between the transformed test points and the given transformed reference point.

At block 312, a corresponding test point in the second space to a given reference point in the first space is deter-mined based on the determined correspondence.

Optionally, one or more reference values of one or more measured parameters at each of the plurality of reference points and each of the corresponding one or more test values of one or more measured parameters may be obtained. The one or more reference values at the given reference point may be compared to the one or more test values obtained at the corresponding test point. In an example, the one or more measured parameters comprises one or more of a principal diffusion component-based parameter, or a diffusion param-eter.

The method as outlined in FIG. 3 is described in more detail with reference to FIGS. 4A to 4C.

FIG. 4A illustrates a simplified abstract representation of the transformation of the reference points and the transfor-mation of the test points into the common space.

FIG. 4B illustrates a simplified abstract representation of determining a correspondence between a transformed test point and a given reference point in the common space.

FIG. 4C illustrates a simplified abstract representation of determining a correspondence between an untransformed test point in the second space and a given untransformed reference point in the first space.

In the examples shown in FIGS. 4A to 4C, the represen-tations of the reference brain and test brain in the first and second space respectively are depicted as originating from a reference subject that is different to the test subject. The one of ordinary skill in the art appreciates that the reference subject and the test subject may be the same subject such that the reference brain and the test brain are the same brain.

Data relating to at least one reference brain is acquired. In the examples shown in FIGS. 4A to 4C, only a single representation of a reference brain and a test brain are depicted. The one or ordinary skill in the art appreciates that the methodologies and techniques as described herein are applicable to at least one reference brain and at least one test brain. By way of example, reference brain data may be acquired from a plurality of different subjects and averaged. In an alternative example, reference brain data may be acquired from a single reference subject at a single time point. In a further alternative example, reference brain data may be acquired from a single reference subject at a plurality of time points.

As described previously, the at least one reference subject may be any human individual. The at least one reference subject may be healthy, in which the at least one reference subject is considered to not have any brain disorders. The at least one reference subject may be non-healthy, in which the at least one reference subject is considered to have a brain disorder or an indication of a least one abnormality in the brain. In an example, the at least one reference brain may be derived from a plurality of reference brains; in this example, the plurality of reference brains may all be healthy, or non-healthy, or a mixture of healthy and non-healthy.

The one of ordinary skill in the art appreciates that the reference brain may be any suitable control brain or derived from a plurality of suitable control reference brains. Fur-thermore, whilst the systems, methods, computer program products and computer readable media as described herein are outlined with respect to a human reference subject, the one of ordinary skill in the art appreciates that the at least one reference subject may be any other suitable mammalian reference subject.

In an embodiment, at least one structural image and a plurality of diffusion-weighted images are acquired for the at least one reference subject. The at least one structural image and the diffusion-weighted images may be acquired in accordance with the acquisition parameters as outlined above. Alternatively, the one of ordinary skill in the art appreciates that any suitable acquisition parameters may be employed in order obtain acquire images with the applicable weighting.

With reference to FIG. 4A, a plurality of reference points in at least one reference brain in a first space 400 are obtained from at least one of the acquired images of the reference brain. The reference points obtained from the reference brain in the first space 400 may be referred to as untransformed reference points. The first space may comprise the native reference subject space.

The circular markers present within the reference brain in the first space 400 are representative of the untransformed reference points. In view of clarity, only one of the circular markers 402a that is representative of one of the plurality of untransformed reference points in the reference brain in the first space 400 is labelled in FIG. 4A. Further, it is appreciated that the number, shape, size, and relative locations of the circular markers are intended to be illustrative.

In an example, the plurality of untransformed reference points are obtained on the basis of cortical profiles generated for the at least one reference subject. Cortical profiles describe lines estimating the columnar axis within the cerebral cortex (McKavanaugh, R. et al. (2019). 'Relating diffusion tensor imaging measurements to microstructural quantities in the cerebral cortex in multiple sclerosis'. Human Brain Mapping. 40(15), pp. 4417-4431; Torso, M. (2020). 'Detection of Alzheimer's Disease using cortical diffusion tensor imaging'. Human Brain Mapping. 42(4), pp. 967-977). The lines allow an estimation of columnar cortical organisation to be calculated. The cortical profiles may be generated according to the techniques as outlined in WO2016162682A1. In an example, the cortical profiles may be derived from determining corresponding vertices on the inner (GM/WM) and outer (pial) surface of the cortex, wherein the correspondence is determined from the original derivation of these surfaces. In an alternative example, the cortical profiles may be generated from a connection defined between a vertex on a given surface to the nearest vertex on the other surface. In an alternative example, as a cortical profile may originate from a given surface along the direction of the surface normal at that point, cortical profiles may be generated on this basis. In still further examples, the cortical profiles may be generated from following curved trajectories defined by solving the Laplace equation or, by any suitable methodology that accounts for the folding of the cortical laminae.

The plurality of untransformed reference points may be obtained from the plurality of lines of the cortical profile that dissect the cortex of the reference brain. In an example, at least 50,000 reference points may be obtained from the plurality of lines dissecting the cortex of the at least one reference brain. In a further example, at least 100,000 reference points may be obtained from the plurality of lines dissecting the cortex of the at least one reference brain. In another example, at least 150,000 reference points may be obtained from the plurality of lines dissecting the cortex of the at least one reference brain. In a still further example, at least 250,000 reference points may be obtained from the plurality of lines dissecting the cortex of the at least one reference brain.

In any of these examples, the plurality of reference points may comprise grey matter surface vertices. In additional or alternative examples, each of the plurality of reference points may be representative of a known marker in the at least one reference brain.

The plurality of untransformed reference points obtained from at least one image of the reference brain are transformed 302 into a common space 404. In an example, the transform is performed according to the transform computed for the reference subject as outlined above. Following the transformation 302, the plurality of reference points may be referred to as transformed reference points.

The common space 404 is intended to act as an abstract representation of a brain. The transformation 302 maps the plurality of reference points for the at least one reference subject to a position or point in the common space 404. In an example, at least 50,000 reference points may be transformed into the common space 404. In a further example, at least 100,000 reference points may be transformed into the common space 404. In another example, at least 150,000 reference points may be transformed into the common space 404. In a still further example, at least 250,000 reference points may be transformed into the common space 404.

In any of these examples, the common space 404 may comprise a substantially spherical space, wherein the common space 404 may resemble a sphere. In this example, the transformation 302 maps each of the untransformed reference points to a point or position on the surface of the sphere.

Data relating to at least one test brain is acquired. In an example, test brain data may be acquired from a single test subject at a single time point. In an alternative example, test brain data may be acquired from a single reference subject at a plurality of time points. In an alternative example, test brain data may be acquired from a plurality of different subjects and averaged.

The at least one test subject may be any human individual. The at least one test subject may be healthy, in which the at least one test subject is considered to not have any brain disorders. The at least one test subject may be non-healthy, in which the at least one test subject is considered to have a brain disorder or an indication of a least one abnormality in the brain. In an example, the at least one test brain may be derived from a plurality of test brains; in this example, the plurality of test brains may all be healthy, or non-healthy, or a mixture of healthy and non-healthy. Whilst the systems, methods, computer program products and computer readable media as described herein are outlined with respect to a human test subject, the one of ordinary skill in the art appreciates that the at least one test subject may be any other suitable mammalian test subject.

In an example, each of the at least one test brain and the at least one reference brain may be the same brain; in this example, the test brain data and the reference brain data may be acquired from the same subject at different time points or in different acquisition cycles at a single time point.

In an embodiment, at least one structural image and a plurality of diffusion-weighted images are acquired for the at least one test subject. The at least one structural image and the diffusion-weighted images may be acquired in accordance with the acquisition parameters as outlined above. Alternatively, the one of ordinary skill in the art appreciates that any suitable acquisition parameters may be employed in order obtain acquire images with the applicable weighting.

A plurality of test points in a test brain in a second space 406 are obtained from at least one of the acquired images of the test brain. The test points obtained from the test brain in the second space 406 may be referred to as untransformed test points. The second space may comprise the native test subject space.

The triangular markers present within the test brain in the second space 406 are representative of the untransformed test points. In view of clarity, only one of the triangular markers 408a representative of one of the plurality of untransformed test points in the test brain in the second space 406 is labelled in FIG. 4A. Further, it is appreciated that the number, shape, size, and relative locations of the triangular markers are intended to be illustrative.

In an example, the plurality of untransformed test points are obtained on the basis of the cortical profiles generated for the at least one test subject according to techniques as described above with reference to the reference subject. The plurality of untransformed test points may be obtained from the plurality of lines of the cortical profile that dissect the cortex of the test brain. In an example, at least 50,000 test points may be obtained from the plurality of lines dissecting the cortex of the test brain. In a further example, at least 100,000 test points may be obtained from the plurality of lines dissecting the cortex of the at least one test brain. In another example, at least 150,000 test points may be obtained from the plurality of lines dissecting the cortex of the at least one test brain. In a still further example, at least 250,000 test points may be obtained from the plurality of lines dissecting the cortex of the at least one test brain.

In any of these examples, the plurality of test points may comprise grey matter surface vertices. In additional or alternative examples, each of the plurality of test points may be representative of a known marker in the test brain.

The plurality of untransformed test points obtained from at least one image of the test brain are transformed 304 into the common space 404. In an example, the transform is performed according to the transform computed for the test subject as outlined above. Following the transformation 304, the plurality of test points may be referred to as transformed test points. Whilst the abstract representation shown in FIG. 4A depicts the test points being transformed into the common space 404 into which the reference points have already been transformed, the one of ordinary skill in the art appreciates that the transformation of the untransformed reference points and untransformed test points may occur in any order. As such, in another example, the untransformed reference points may be transformed into the common space into which the test points have already been transformed.

As previously described, the common space 404 is intended to act as an abstract representation of a brain. The transformation maps the plurality of test points for the at least one test subject to a position or point in the common space 404. In an example, at least 50,000 test points may be transformed into the common space 404. In a further example, at least 100,000 test points may be transformed into the common space 404. In an additional further example, at least 150,000 test points may be transformed into the common space 404. In a still further example, at least 250,000 test points may be transformed into the common space 404.

As described previously, in any of these examples, the common space 404 may comprise a substantially spherical space, wherein the common space 404 may resemble a sphere. The transformation 304 maps each of the untransformed test points to a position or point on the surface of the sphere.

FIG. 4B illustrates a simplified abstract representation of determining a correspondence between a transformed test point and a given reference point in the common space.

A position of each of the transformed reference points and transformed test points is determined 306 in the common space 404. The common space 404 has a plurality of positions or points. The one of ordinary skill in the art appreciates that each of the plurality of positions in the common space may be defined by a set of coordinates. The determination of the position of each of the transformed reference points and each of the transformed test points may comprise determining respective sets of reference coordinates and test coordinates for the transformed reference points and test points.

By way of example, at step 306 in FIG. 4B, the common space 404 has a plurality of positions as defined by the major lines of the grid. The one of ordinary skill in the art appreciates that the grid is illustrative only. As such, minor grid lines may be also envisaged. Other means of defining positions may also be envisaged. In these examples, each of the plurality of positions may be represented by a set of coordinates within the grid. Based on the predefined positions, a position in the grid of each of the transformed reference points and transformed test points can be determined. In this way, a position of each of the transformed reference points and each of the transformed test points in the common space 404 can be inferred.

In an example, the common space 404 may be a substantially spherical space resembling a sphere and the transformation steps 302 and 304 map the untransformed reference points and untransformed test points to the substantially spherical surface. Based on the relative location of the transformed reference points and transformed test points to the predefined points on the surface of the sphere, a position of each of the transformed references points and transformed test points can be determined on the surface of the sphere.

A displacement of each of the transformed reference points relative to each of the transformed test points based on the determined positions is determined 308. In view of clarity, the double-headed arrows at step 308 in FIG. 4B show the calculation of the displacement between three sets of transformed reference points and transformed test points only. In an example, the displacement between each of the transformed reference points relative to each of the transformed test points is determined by calculating an offset between each set of test coordinates and each set of reference coordinates. In this example, the double-headed arrows at step 308 in FIG. 4B describe the offset between the three sets of transformed reference points and transformed test points. The one of ordinary skill in the art appreciates that an offset can be calculated between each transformed reference point and each transformed test point.

A correspondence between one of the transformed test points and a given transformed reference point is determined 310 based on the calculated displacements. By way of example, at step 310 in FIG. 4B, a correspondence between the given transformed reference point 402b and transformed test point 408b is determined.

As described previously, the relative position of each of the transformed test points to each of the transformed reference points may be determined by calculating an offset between each set of test coordinates and each set of reference coordinates that define the respective positions of the transformed test points and transformed reference points in the common space 404. The correspondence between the transformed test point 408b to the given transformed reference point 402b may be determined by determining that the test coordinates defining the position of transformed test point 408b have a minimum offset relative to the set of reference coordinates defining the position of reference point 402b. In other words, the displacement between transformed reference point 402b and all of the transformed test points is calculated. The displacement may be determined by calculating an offset between the reference coordinates describing the position of transformed reference point 402b in common space 404 and each set of test coordinates describing a position of each transformed test point in the common space 404. The correspondence between transformed test point 408b and transformed reference point 402b may be determined by determining that the offset between transformed test point 408b and transformed reference point 402b describes the smallest displacement between transformed reference point 408b to any of the transformed test points.

FIG. 4C illustrates a simplified abstract representation of determining a correspondence between an untransformed test point in the second space and a given untransformed reference point in the first space.

A corresponding untransformed test point 408a in the second space to a given untransformed reference point 402a in the first point is determined 312. This is based on the determined correspondence between the transformed test point 408b and transformed reference point 402b in the common space. As described previously, transforms are calculated to map the untransformed reference points and untransformed test points from their respective first and second spaces into the common space 404. Owing to the calculated transforms, the relationship between each untransformed reference point and each untransformed test point and their respective transformed counterpart points is known. As a consequence, the correspondence between the untransformed test point and untransformed reference point can be inferred in the respective subject spaces based on the determined correspondence in the common space.

With reference to FIG. 4B, the correspondence between transformed test point 408b and given transformed reference point 402b in the common space 404 is determined. In FIG. 4C, a correspondence between the untransformed test point 408a and untransformed reference point 402a is determined based on the determined correspondence between the equivalent transformed points in the common space.

This methodology allows for the determination of substantially equivalent points in the at least one reference brain and the at least one test brain. In an example, each of the plurality of reference points is representative of a known marker in the reference brain, and each of the plurality of test points is representative of a known marker in the test brain. By determining the substantially equivalent points in the reference brain and in the test brain, the same known marker in the reference brain and the test brain is identifiable.

Optionally, one or more reference values of one or more measured parameters at each of the plurality of reference points and corresponding one or more test values of one or more measured parameters at each of the plurality of test points may be obtained.

Applying the methodology as outlined above, in a specific non-limiting example, the following steps were undertaken. A reference brain was selected, in this instance from Freesurfer. A plurality of reference points in the first, reference space were identified. In this example, the reference points comprised surface vertices. Test brains from four different test subjects were obtained. A plurality of test points in the second, test space in each of the test brains were identified. In this example, the test points comprised test vertices. The aim was to map from the reference brain vertex index in the reference space to the test brain vertex index in the test space.

The reference points and test points were transformed into a common space. In this example, the common space was a substantially spherical space. A position of each of the transformed reference points and each of the transformed test points in the common space was determined. In this example, the relative positions of the transformed test points and transformed reference points were assumed to represent an analogue position on the cortex, providing the given positions occupied the same brain region.

A displacement between each of the transformed test points relative to each of the transformed reference points based on the determined positions was calculated. A correspondence between one of the transformed test points and a given transformed reference point based on the calculated displacements. In this example, the correspondence was determined by determining the transformed test point that has the minimum Euclidean distance to a given transformed reference point. Based on this minimal distance, a corresponding test point in the second space to a given reference point in the first space was determined.

Figure 5A:
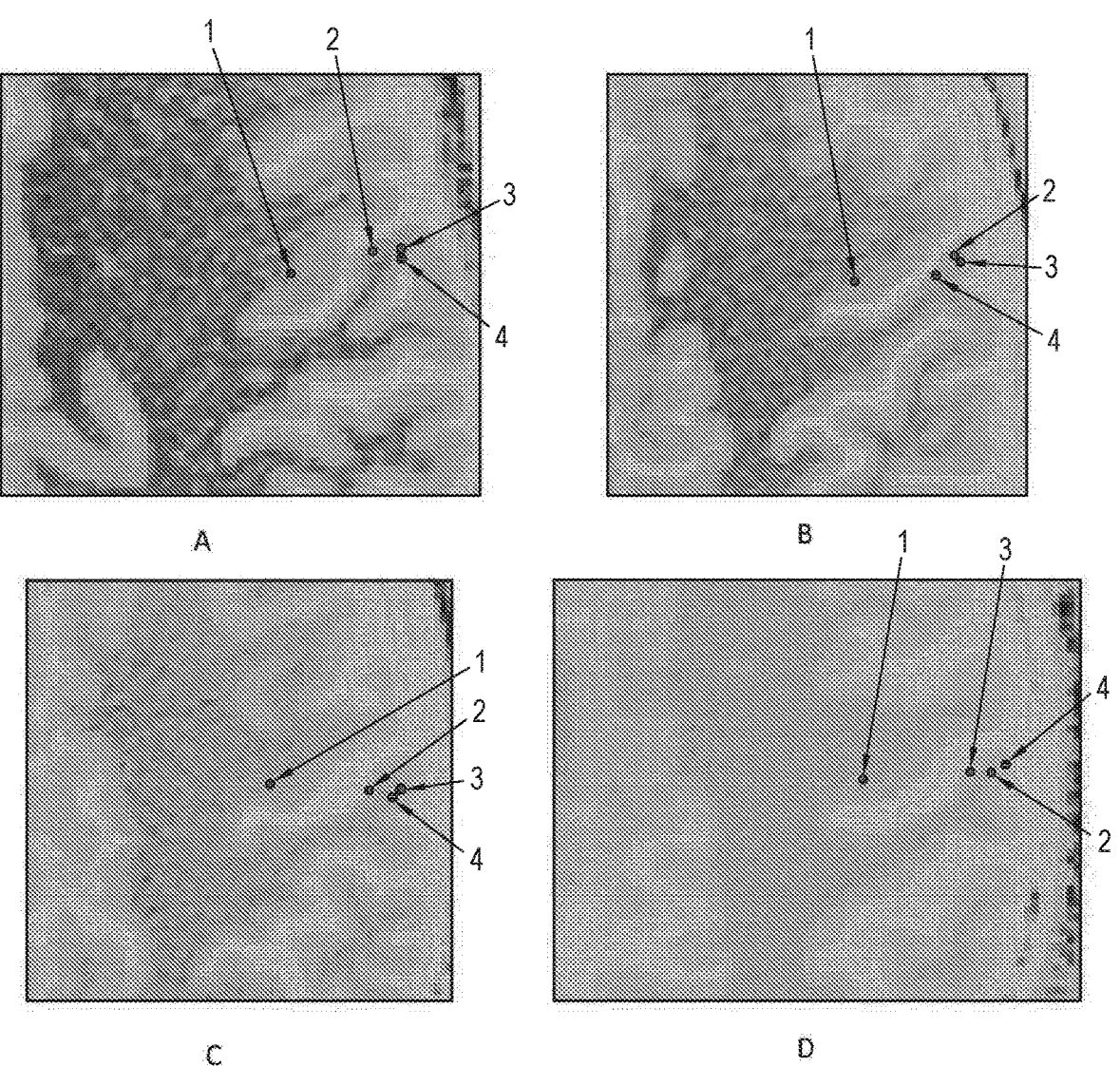
FIGS. 5A to 5C illustrate a specific example of the described methodology in use.
Figure 5B:
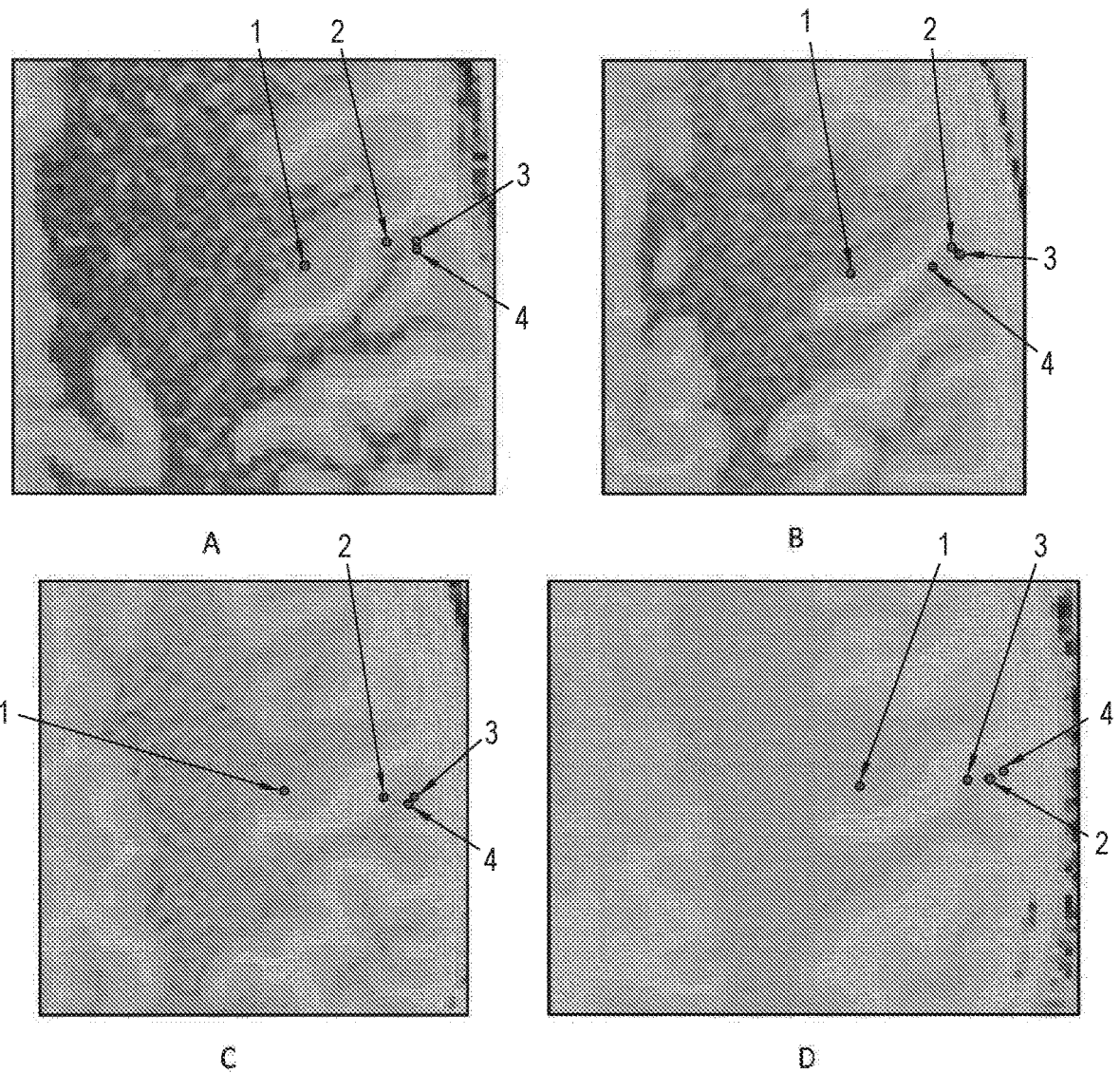
Figure 5C:
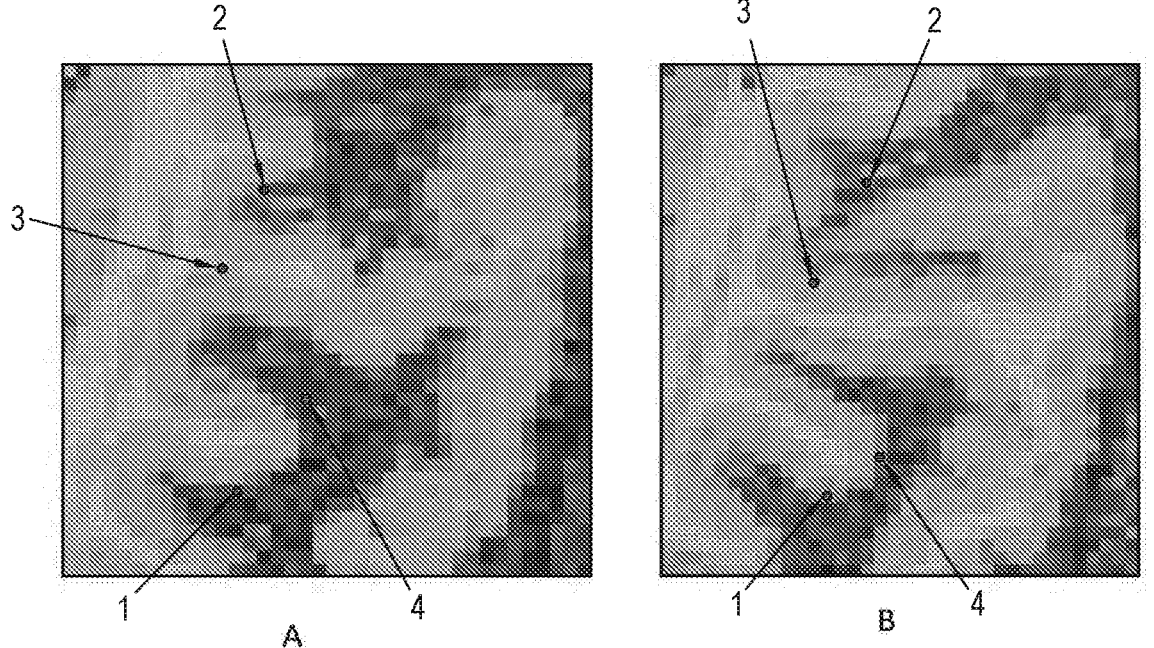

The output of the applied methodology as outlined above is depicted in FIG. 5A. FIG. 5A illustrates four test brains A, B, C, and D respectively. Arrows 1, 2, 3, and 4 denote substantially equivalent test points in each of the test brains e.g., arrow 1 is illustrative of the same test point in each of the four brains. FIG. 5B provides another demonstration of the applied methodology, wherein arrows 1, 2, 3, and 4 are again representative of substantially equivalent test points in the four test brains, A, B, C, and D. FIG. 5C provides a further example, wherein arrows 1, 2, 3, and 4 are demonstrative of substantially equivalent test points in test brains A and B.

The outputs are as expected, depicting the mapping that allows the identification of substantially equivalent test points and reference points. As substantially equivalent reference points and test points are able to be determined in their respective subject spaces, estimates of the obtained parameter values at the respective points are directly comparable, enabling possible pathology in a given test brain to be evaluated.

Figure 6:
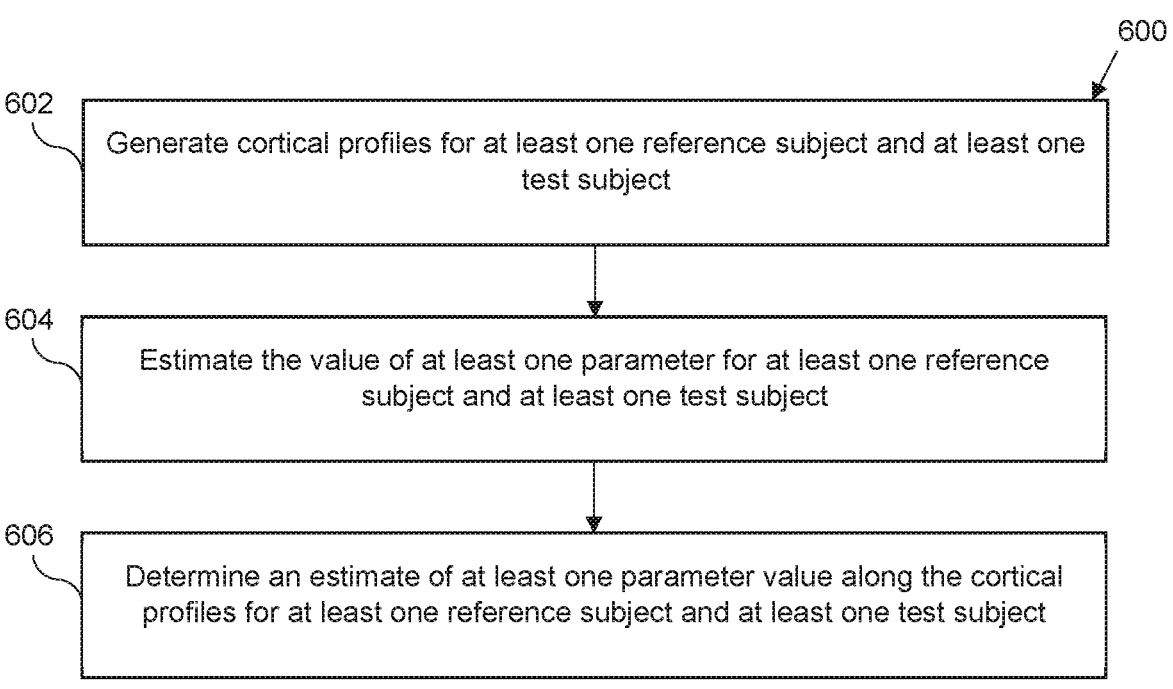
FIG. 6 illustrates an exemplary method for performing cortical diffusivity analyses.

FIG. 6 illustrates an exemplary method 600 for performing cortical diffusivity analyses for at least one reference subject and at least one test subject.

At block 602, cortical profiles may be generated for at least one reference subject and at least one test subject. Cortical profiles describe lines estimating the columnar axis within the cerebral cortex. The lines allow an estimation of columnar cortical organisation to be calculated. As described previously, the cortical profiles may be generated according to the techniques as outlined in WO2016162682A1. In an example, the cortical profiles may be derived from determining corresponding vertices on the inner (GM/WM) and outer (pial) surface of the cortex, wherein the correspondence is determined from the original derivation of these surfaces. In an alternative example, the cortical profiles may be generated from a connection defined between a vertex on a given surface to the nearest vertex on the other surface. In an alternative example, as a cortical profile may originate from a given surface along the direction of the surface normal at that point, cortical profiles may be generated on this basis. In still further examples, the cortical profiles may be generated from following curved trajectories defined by solving the Laplace equation or, by any suitable methodology that accounts for the folding of the cortical laminae.

At block 604, statistical analyses of the processed diffusion images may be performed for at least one test subject and at least one reference subject. Estimates of the value of one or more parameters may be obtained. The one or more measured parameter may comprise at least one of a principal diffusion component-based parameter, a minicolumn-based parameter, or a diffusion-based parameter.

In an example, estimates of at least one principal diffusion component-based parameter may be obtained in the at least one reference brain and the at least one test brain. The principal diffusion component-based parameter may comprise at least one of an angle of deviation in a between the principal diffusion direction and at least one columnar direction of a vertical column through the cortical layer of the brain, perpendicular diffusivity or parallel diffusivity.

The angle of deviation, known as AngleR, relates to the angular deviation between the columnar direction in the cortical grey matter and the principal diffusion direction. As a consequence, it is measurable only in grey matter voxels.

Perpendicular diffusivity, known as PerpPD (D1,⊥[×10⁻³ mm²/s]), relates to the projection of the principal diffusion vector component on to the plane perpendicular to the radial columnar direction across the cortex.

Parallel diffusivity, known as ParlPD (parallel diffusivity D1,∥[×10⁻³ mm²/s]) relates to the projection of the principal diffusion vector component on to the plane parallel to the radial columnar direction across the cortex.

PerpPD and ParlPD are calculated by multiplying the principal eigenvector and its corresponding eigenvalue value. The multiplied value is resolved into components; the perpendicular component is representative of PerpPD, whilst the parallel component is representative of ParlPD.

In additional or alternative examples, estimates of at least one minicolumn-based parameter may be obtained in the at least one reference brain and the at least one test brain. Minicolumns relate to vertical columns through the cortical layers of the brain. The minicolumn-based parameter may comprise at least one of a minicolumn width, a minicolumn spacing, an axonal fibre bundle width, an axonal fibre bundle spacing, a dendritic fibre bundle width, a dendritic fibre bundle spacing, a minicolumn core width, or a minicolumn peripheral neuropil space.

Minicolumn width relates to the width of the minicolumn core and half of the peripheral neuropil space on either side of the minicolumn core.

Minicolumn spacing relates to the relative centre-to-centre spacing of minicolumns.

Axonal fibre bundle width relates to the width of axonal bundles associated with each minicolumn.

Axonal fibre bundle spacing relates to the centre-to-centre spacing of axonal bundles.

Dendritic fibre bundle width relates to the width of dendrite bundles that extend vertically, in the direction of minicolumns, through the cerebral cortex.

Dendritic fibre bundle spacing relates to the spacing of dendritic fibre bundles.

Minicolumn core width relates to the part of the column that contains 90% of the cell bodies.

Minicolumn peripheral neuropil space relates to the surrounding neuropil which, along with the minicolumn core, makes up the minicolumn. As such, the minicolumn peripheral neuropil space is calculable by subtracting the measure of the minicolumn core from the value of the minicolumn width.

In additional or alternative examples, whole brain voxel-wise estimates of the values of at least one diffusion-based parameter may be determined for at least one test subject and at least one reference subject. Additionally or alternatively, region-of-interest estimates of the values of at least one diffusion-based parameter may be determined for at least one reference subject and at least one test subject. The diffusion-based parameter may comprise at least one of mean minicolumn diffusivity, mean diffusivity, fractional anisotropy, radial diffusivity, or axial diffusivity.

Minicolumn diffusivity relates to the combination of diffusion components across multiple diffusion directions that are perpendicular to the radial direction across the cortex. The mean minicolumn diffusivity is calculable by combining the components of the eigenvalues that are perpendicular to the radial direction across the cortex.

Mean diffusivity is a measure of the overall diffusivity that occurs within a voxel and is calculated by computing an average of the three eigenvalues within the given voxel.

Fractional anisotropy relates to a measure of the directionality of the diffusion process within a voxel and is measured as a scalar value between zero and one, wherein zero represents isotropic diffusion, whilst one represents anisotropic diffusion.

Radial diffusivity relates to diffusivity perpendicular to the axonal fibres in the brain. Radial diffusivity can be described by an average of the two minor eigenvalues of the diffusion tensor.

Axial diffusivity relates to diffusivity parallel to the axonal fibres in the brain. Axial diffusivity can be described by the principal eigenvalue of the diffusion tensor.

At block 606, an estimate of a value of at least one parameter along the cortical profiles may be determined for the at least one reference subject and the at least one test subject. The parameter may be at least one of the diffusion parameters, the principal diffusion component-based parameters, or the minicolumn-based parameters as described above. An estimate of any of these parameter values may be determined along the cortical profiles across the whole brain and/or within at least one region of interest.

By way of example, an estimate of mean diffusivity along the cortical profiles across the whole brain may be calculated for at least one reference subject and at least one test subject. As described above, mean diffusivity relates to the measure of the total diffusion that occurs within a voxel. The mean mean diffusivity value along the cortical profile may be calculated by determining a weighted average of each of the mean diffusivity values along the given cortical profiles across the whole brain. Additionally or alternatively, an estimate of mean diffusivity along the cortical profiles within a given ROI may be calculated. The mean mean diffusivity value along the cortical profile(s) within the given ROI may be calculated by determining a weighted average of the mean diffusivity values along the cortical profile(s) across the given ROI.

By way of an additional example, estimates of at least one of the principal diffusion component-based parameters may be calculated along the cortical profiles across the whole brain and/or within at least one ROI for at least one reference subject and at least one test subject. In more detail and by way of example, an estimate of AngleR along the cortical profiles across the whole brain may be calculated by determining an average of the AngleR parameter values along the cortical profiles across the whole brain. Additionally or alternatively, an estimate of AngleR along the cortical profile(s) across at least one given ROI may be calculated by determining an average of the AngleR parameter values along the cortical profile(s) across the given ROI.

Optionally, estimates of at least one of the parameter values may be obtained at any of the reference points and test points. As substantially equivalent reference points and test points are determined in their respective subject spaces, the estimates of the obtained parameter values are directly comparable.

Owing to this, the parameter estimates are more comprehensive and provide a more informative indication of the underlying diffusion processes within the brain. The ability to perform direct comparisons in corresponding locations across subjects allows researchers and clinicians to further explore the relationship between diffusivity and cognitive function. This can allow deviations in the test brain to be detected, thereby allowing inferences on prognosis and diagnosis of brain disorders to be made, along with allowing indications regarding brain injury and brain health to be determined. A deviation in the test brain could comprise at least one of a disorder, an injury, or an indication of brain health.

In an example, a deviation in the test brain can be detected, enabling inferences regarding a prognosis to be made. For example, the comparison of the estimated parameter value at the given untransformed reference point to the sister estimate obtained at the corresponding untransformed test point may allow indication of a prognosis of at least one disorder in the test brain to be obtained. In more detail, the prognosis of at least one disorder in the test brain may be determined by detecting the difference in the one or more test value at the given test point relative to the corresponding reference value at the corresponding reference point, wherein the difference exceeds, or is lower than, a predetermined threshold difference.

Optionally, at least one therapeutic to be administered may be determined based on the detected indication of the prognosis of at least one disorder. The therapeutic may be a pharmacological treatment such as: a small molecule drug; a biologic (for example, an antibody); or a polynucleotide (DNA and/or RNA) delivered by suitable vector or particle.

Optionally, at least one non-pharmacological treatment to be implemented may be determined based on the detected indication of the prognosis of at least one disorder. A non-pharmacological treatment may encompass an intervention that is not based on the administration of a medication. A non-pharmacological treatment may comprise cognitive stimulation therapy, cognitive rehabilitation, cognitive behavioural therapy, physiotherapy, speech and language therapy, deep brain stimulation, occupational therapy, or variations in lifestyle such as changes to sleep, exercise, and/or dietary habits.

Additionally or alternatively, the comparison of the estimated parameter value at the given untransformed reference point to the sister estimate obtained at the corresponding untransformed test point may allow an indication of a presence of at least one disorder in the test brain to be determined. In more detail, an indication of a presence of at least one disorder in the test brain may be determined by detecting the difference in the one or more test value at the given test point relative to the corresponding reference value at the corresponding reference point, wherein the difference exceeds, or is lower than, a predetermined threshold difference.

Optionally, at least one therapeutic to be administered may be determined based on the detected indication of the presence of at least one disorder. The therapeutic may be a pharmacological treatment such as: a small molecule drug; a biologic (for example, an antibody); or a polynucleotide (DNA and/or RNA) delivered by suitable vector or particle.

Optionally, at least one non-pharmacological treatment to be implemented may be determined based on the detected indication of the presence of at least one disorder. A non-pharmacological treatment may encompass an intervention that is not based on the administration of a medication. A non-pharmacological treatment may comprise cognitive stimulation therapy, cognitive rehabilitation, cognitive behavioural therapy, physiotherapy, speech and language therapy, deep brain stimulation, occupational therapy, or variations in lifestyle such as changes to sleep, exercise, and/or dietary habits.

In any of the above examples, the at least one disorder may comprise a neurodegenerative disorder, a neuroinflammatory disorder, a neurodevelopmental disorder, a psychiatric disorder, or a brain disorder associated with a SARS-CoV-2 infection. In more detail, the at least one disorder may comprise Alzheimer's Disease, cerebrovascular dementia, mild cognitive impairment, frontotemporal dementia, dementia with Lewy Bodies, autism, an autism spectrum disorder, multiple sclerosis, epilepsy, amyotrophic lateral sclerosis, Parkinson's disease, schizophrenia, bipolar disorder, dyslexia, Down's syndrome, Huntington's disease, prion disease, depression, obsessive-compulsive disorder, attention deficit hyperactivity disorder, or chronic traumatic encephalopathy.

Additionally or alternatively, the comparison of the estimated parameter value at the given untransformed reference point to the sister estimate obtained at the corresponding untransformed test point may allow an indication of at least one injury in the test brain to be determined. In more detail, an indication of at least one injury in the test brain may be determined by detecting the difference in the one or more test value at a given test point relative to the corresponding reference value at the corresponding reference point, wherein the difference exceeds, or is lower than, a predetermined threshold difference.

Optionally, at least one therapeutic to be administered may be determined based on the detected indication of the at least one injury. The therapeutic may be a pharmacological treatment such as: a small molecule drug; a biologic (for example, an antibody); or a polynucleotide (DNA and/or RNA) delivered by suitable vector or particle.

Optionally, at least one non-pharmacological treatment to be implemented may be determined based on the detected indication of the at least one injury. A non-pharmacological treatment may encompass an intervention that is not based on the administration of a medication. A non-pharmacological treatment may comprise cognitive stimulation therapy, cognitive rehabilitation, cognitive behavioural therapy, physiotherapy, speech and language therapy, deep brain stimulation, occupational therapy, or variations in lifestyle such as changes to sleep, exercise, and/or dietary habits.

In an example, the at least one injury may comprise a mild traumatic brain injury, a concussion, a cerebral contusion, an anoxic brain injury, or a hypoxic brain injury.

Additionally or alternatively, the comparison of the estimated parameter value at the given untransformed reference point to the sister estimate obtained at the corresponding untransformed test point may allow a measure of brain health in the test brain to be determined. In more detail, a measure of brain health in the test brain may be determined by detecting the difference in the one or more test value at a given test point relative to the corresponding reference value at the corresponding reference point, wherein the difference exceeds, or is lower than, a predetermined threshold difference. Brain Health is described by the World Health Organisation as a concept that encompasses neural development, plasticity, functioning, and recovery across the life course (Who.int. 2022. *Brain health*. [online] Available at: <https://www.who.int/health-topics/brain-health#tab=tab_1> [Accessed 13 Jul. 2022]). The one of ordinary skill in the art appreciates that there are number of measures that may be used to describe brain health, and/or to act as a representative hallmark of brain health under this definition.

Optionally, at least one therapeutic to be administered may be determined based on the determined measure of brain health. The therapeutic may be a pharmacological treatment such as: a small molecule drug; a biologic (for example, an antibody); or a polynucleotide (DNA and/or RNA) delivered by suitable vector or particle.

Optionally, at least one non-pharmacological treatment to be implemented may be determined based on the determined measure of brain health. A non-pharmacological treatment may encompass an intervention that is not based on the administration of a medication. A non-pharmacological treatment may comprise cognitive stimulation therapy, cognitive rehabilitation, cognitive behavioural therapy, physiotherapy, speech and language therapy, deep brain stimulation, occupational therapy, or variations in lifestyle such as changes to sleep, exercise, and/or dietary habits.

The methodology and techniques as described herein allow the same number of sample points to be determined across all subjects. Additionally, the methodology and techniques as described herein ensure that the positions of the sample points are the same across all subjects. This results in a much higher degree of comparability between individual sample points across subjects. Owing to this, the measurement of parameters at each of the sample points is more consistent such that subsequent analyses of such parameters are more reliable accurate, and comprehensive.

Figure 7:
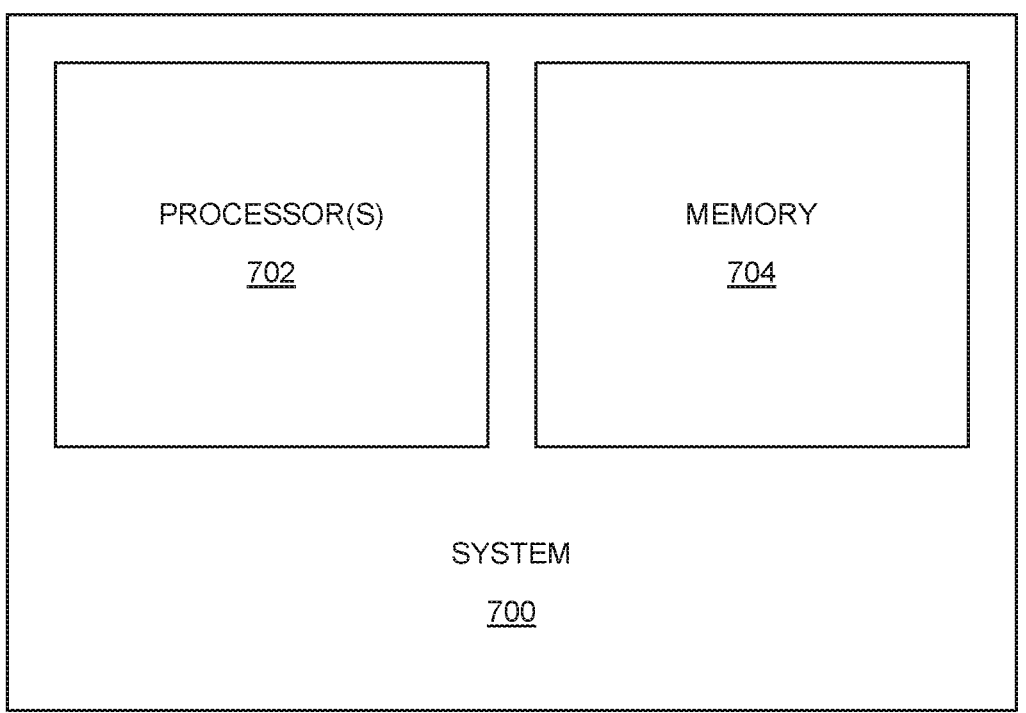
FIG. 7 depicts an exemplary system implementable according to aspects of the present technology.

FIG. 7 depicts an exemplary system 700 implementable according to aspects of the present technology. System 700 comprises one or more processors 702 and a memory 704. The one or more processors 702 may be configured to execute instructions read from the memory 704.

The memory 704 may include computer-readable media. Computer readable media may be any available media that is accessible on a computer system and may comprise computer storage media and communication media. Computer storage media may comprise RAM, ROM, EEPROM, random-access memory (RAM), read-only memory (ROM), electrically erasable programmable read-only memory (EE-PROM), flash memory, phase change memory (PRAM), statis random-access memory (SRAM), dynamic random-access memory (DRAM), flash memory, compact disk read-only memory (CD-ROM), digital versatile disks (DVD) or other optical storage, magnetic disk storage, magnetic tape or any other suitable medium that is useable to store data for access by a computer system. Communication media may comprise computer-readable instructions, data structures, program modules or data modulated in a data signal.

Any of the acts of any of the methods described herein may be implemented by the one or more processors configured with executable instructions that may be stored in the memory or on one or more computer-readable media.

Although FIG. 7 shows an exemplary system 700, it will be understood that other computing systems with varying aspects and components may be used.

The non-transitory computer-readable medium may have stored thereon a set of instruction which, when executed, cause the at least one processor to perform any of the acts of any of the methods as described herein.

The present technology may be implemented using computer programming techniques and through the use of software, hardware or firmware, or through any suitable combination of these. A program having computer-readable instructions may be provided within computer-readable media, resulting in a computer program product, implementable according to aspects of the present technology.

FIG. 8 illustrates an exemplary method 800 of treatment according to aspects of the present invention.

Method 300 is performed as described previously with respect to FIG. 3.

At block 802, one or more reference values of one or more measured parameters at each of the plurality of reference points are obtained.

At block 804, corresponding one or more test values of one or more measured parameters at each of the plurality of test points are obtained.

At block 806, the one or more reference values at the given reference point to the one or more test values obtained at the corresponding test point are compared.

At block 808, an indication of a presence of at least one disorder in the test brain based on the comparison of the one or more reference values at the given reference point to the one or more test values obtained at the corresponding test point is detected.

Additionally or alternatively, an indication of a prognosis of at least one disorder in the test brain based on the comparison of the one or more reference values at the given reference point to the one or more test values obtained at the corresponding test point is detected. The at least one disorder may a neurodegenerative disorder, a neuroinflammatory disorder, a neurodevelopmental disorder, a psychiatric disorder, or a brain disorder associated with a SARS-COV-2 infection. Further, the at least one disorder may comprise Alzheimer's Disease, cerebrovascular dementia, mild cognitive impairment, frontotemporal dementia, dementia with Lewy Bodies, autism, an autism spectrum disorder, multiple sclerosis, epilepsy, amyotrophic lateral sclerosis, Parkinson's disease, schizophrenia, bipolar disorder, dyslexia, Down's syndrome, Huntington's disease, prion disease, depression, obsessive-compulsive disorder, attention deficit hyperactivity disorder, or chronic traumatic encephalopathy.

Additionally or alternatively, an indication of at least one injury in the test brain based on the comparison of the one or more reference values at the given reference point to the one or more test values obtained at the corresponding test point is detected. The at least one injury may comprise a mild traumatic brain injury, a concussion, a cerebral contusion, an anoxic brain injury, or a hypoxic brain injury.

Additionally or alternatively, a measure of brain health in the test brain based on the comparison of the one or more reference values at the given reference point to the one or more test values obtained at the corresponding test point is determined.

At block 810, at least one therapeutic to be administered based on the detected indication of the presence of at least one disorder is determined. In an additional or alternative examples, at least one non-pharmacological treatment to be implemented based on the detected indication of the presence of the at least one disorder is determined.

Additionally or alternatively, at least one therapeutic to be administered based on the detected indication of the prognosis of at least one disorder is determined.

In an additional or alternative examples, at least one non-pharmacological treatment to be implemented based on the detected indication of the prognosis of the at least one disorder is determined.

Additionally or alternatively, at least one therapeutic to be administered based on the detected indication of at least one injury is determined.

In an additional or alternative examples, at least one non-pharmacological treatment to be implemented based on the detected indication of the at least one injury is determined.

Additionally or alternatively, at least one therapeutic to be administered based on the measure of brain health is determined.

In an additional or alternative examples, at least one non-pharmacological treatment to be implemented based on the measure of brain health is determined.

At block 812, the at least one therapeutic is administered. In an additional or alternative examples, at least one non-pharmacological treatment is implemented.

In an example, the at least one disorder may comprise Alzheimer's disease. The at least one therapeutic to be administered may comprise a cholinesterase inhibitor, an N-methyl-D-aspartate (NMDA) antagonist, or a monoclonal antibody. A cholinesterase inhibitor may comprise donepezil, rivastigmine, or galantamine. Donepezil, rivastigmine, and galantamine all act to prevent the breakdown of acetylcholine in the brain. Rivastigmine further acts to prevent the breakdown of butyrylcholine in the brain, whilst galantamine also stimulates receptors to allow an increase in the release of acetylcholine. Memantine is a type of NMDA antagonist that acts to block the effects of glutamate. Aducanumab is a monoclonal antibody that targets amyloid beta in the brain. Additionally or alternatively, at least one non-pharmacological treatment may be implemented including cognitive stimulation therapy, cognitive rehabilitation, or cognitive behavioural therapy.

In an example, the at least one disorder may comprise Parkinson's disease. The at least one therapeutic to be administered may comprise a central nervous system agent, a decarboxylase inhibitor, a dopamine agonist, a monoamine oxidase-B (MAO-B) inhibitor, a catechol-O-methyltransferase (COMT) inhibitor, or an adamantane. Levodopa is a central nervous system agent that is a precursor to dopamine, allowing it to be metabolised to dopamine. Carbidopa is a decarboxylase inhibitor that prevents the breakdown of levodopa until it reaches the brain. Dopamine agonists such as apomorphine act as a dopamine substitute in the brain. A MAO-B inhibitors may comprises selegiline or rasagiline. MAO-B inhibitors act to inhibit the effect of MAO-B which break downs dopamine in the brain. COMT inhibitors act to limit the breakdown of levodopa by COMT. Amantidine is a type of adamantane that is intended to target the dyskinetic symptoms of Parkinson's disease. Additionally or alternatively, at least one non-pharmacological treatment may be implemented including physiotherapy, speech and language therapy, deep brain stimulation, or occupational therapy.

Clauses

Alternatively, or in addition to the other examples described herein, further examples include:

Clause A. A computer-implemented method comprising: transforming, into a common space, a plurality of reference points obtained from at least one image of a reference brain in a first space; transforming, into the common space, a plurality of test points obtained from at least one image of a test brain in a second space; determining a position of each of the transformed reference points and each of the transformed test points in the common space; calculating a displacement of each of the transformed test points relative to each of the transformed reference points based on the determined positions; determining a correspondence between one of the transformed test points and a given transformed reference point based on the calculated displacements; and determining a corresponding test point in the second space to a given reference point in the first space based on the determined correspondence.

Clause B. The computer-implemented method of clause A, wherein determining the correspondence between one of the transformed test points and the given transformed reference point further comprises determining the transformed test point having a minimum displacement relative to the given transformed reference point Clause C. The computer-implemented method of clause A or B, wherein determining the position in the common space of each of the transformed reference and test points further comprises determining respective sets of reference coordinates and test coordinates for the transformed reference points and test points.

Clause D. The computer-implemented method of clause D, wherein calculating the displacement of each of the transformed test points relative to each of the transformed reference points further comprises calculating an offset between each set of test coordinates and each set of reference coordinates.

Clause E. The computer implemented method of any of clauses C or D, wherein determining the correspondence between one of the transformed test points and the given transformed reference point further comprises determining the set of test coordinates having a minimum offset relative to the set of reference coordinates of the given transformed reference point.

Clause F. The computer-implemented method of any of clauses C to E, wherein the set of reference coordinates and the set of test coordinates comprise at least one of Cartesian coordinates or radial coordinates.

Clause G. The computer-implemented method of any of clauses A to F further comprising: obtaining one or more reference values of one or more measured parameters at each of the plurality of reference points; and obtaining corresponding one or more test values of one or more measured parameters at each of the plurality of test points.

Clause H. The computer-implemented method of clause G, further comprising comparing the one or more reference values at the given reference point to the one or more test values obtained at the corresponding test point.

Clause I. The computer-implemented method of clause G or H, wherein the one or more measured parameters comprises at least one of a principal diffusion component-based parameter, a minicolumn-based parameter or a diffusion parameter.

Clause J. The computer-implemented method of clause I, wherein the principal diffusion component-based parameter comprises at least one of an angle of deviation between the principal diffusion direction and a columnar direction of a vertical column through the cortical layer of the brain, perpendicular diffusivity or parallel diffusivity, the minicolumn-based parameter comprises at least one of a minicolumn width, a minicolumn spacing, an axonal fibre bundle width, an axonal fibre bundle spacing, a dendritic fibre bundle width, a dendritic fibre bundle spacing, a minicolumn core width, or minicolumn peripheral neuropil space, and the diffusion parameter comprises at least one of mean minicolumn diffusivity, radial diffusivity, fractional anisotropy, mean diffusivity or axial diffusivity.

Clause K. The computer-implemented method of any of clauses H to J, further comprising obtaining an indication of a prognosis of at least one disorder in the test brain based on the comparison of the one or more reference values at the given reference point to the one or more test values obtained at the corresponding test point.

Clause L. The computer-implemented method of any of clauses H to K, further comprising detecting an indication of a presence of at least one disorder in the test brain based on the comparison of the one or more reference values at the given reference point to the one or more test values obtained at the corresponding test point.

Clause M. The computer-implemented method of clause L, further comprising determining at least one therapeutic to be administered based on the detected indication of the at least one disorder.

Clause N. The computer-implemented method of any of clauses K to M, wherein the disorder comprises at least one of Alzheimer's Disease, cerebrovascular dementia, mild cognitive impairment, frontotemporal dementia, dementia with Lewy Bodies, autism, an autism spectrum disorder, multiple sclerosis, epilepsy, amyotrophic lateral sclerosis, Parkinson's disease, schizophrenia, bipolar disorder, dyslexia, Down's syndrome, Huntington's disease, prion disease, depression, obsessive-compulsive disorder and attention deficit hyperactivity disorder.

Clause O. The computer-implemented method of any of clauses A to N, wherein the at least one image of the reference brain comprises at least one of a brain atlas, an image of a control brain or a second image of the test brain, wherein the control brain comprises a different brain to the test brain.

Clause P. The computer-implemented method of any of clauses A to O, wherein the common space is a substantially spherical space.

Clause Q. The computer-implemented method of any of clauses A to P, wherein the reference points and the test points comprise grey matter surface vertices.

Clause R. The computer-implemented method of any of clauses A to Q, wherein each of the plurality of reference points is representative of a known marker in the reference brain, and each of the plurality of test points is representative of a known marker in the test brain.

Clause S. A system comprising: at least one processor; and memory storing computer-executable instructions that, when executed by the one or more processors, cause the at least one processor to: transform, into a common space, a plurality of reference points obtained from at least one image of a reference brain in a first space; transform, into the common space, a plurality of test points obtained from at least one image of a test brain in a second space; determine a position of each of the transformed reference points and each of the transformed test points in the common space; calculate a displacement of each of the transformed test points relative to each of the transformed reference points based on the determined positions; determine a correspondence between one of the transformed test points and a given transformed reference point based on the calculated displacements; and determine a corresponding test point in the second space to a given reference point in the first space based on the determined correspondence.

Clause T. A computer program product comprising instructions which, when the program is executed by a computer, cause the computer to carry out the method of any one of clauses A to R.

Clause U. A computer-readable medium comprising instructions which, when executed by a computer, cause the computer to carry out the method of any one of clauses A to R.

Clause V. A method of treatment comprising: performing the method according to clause M and thereby determining that at least one therapeutic is to be administered; and administering said at least one therapeutic.

The invention claimed is:

1. A computer-implemented method comprising:

transforming, into a common space, a plurality of reference points obtained from at least one image of a reference brain in a first space, wherein each of the reference points comprise a plurality of surface vertices, each associated with a vertex index;

transforming, into the common space, a plurality of test points obtained from at least one image of a test brain in a second space wherein each of the test points comprise a plurality of surface vertices, each associated with a surface index;

determining a position of each of the transformed reference points and each of the transformed test points in the common space;

calculating a displacement of each of the transformed test points relative to each of the transformed reference points based on the determined positions;

determining a correspondence between one of the transformed test points and a given transformed reference point based on the calculated displacements, wherein determining the correspondence between one of the transformed test points and the given transformed reference point further comprises determining the transformed test point having a minimum displacement relative to the given transformed reference point;

determining a corresponding test point in the second space to a given reference point in the first space based on the determined correspondence;

obtaining one or more reference values of one or more measured parameters at each of the plurality of reference points; and obtaining corresponding one or more test values of one or more measured parameters at each of the plurality of test points, wherein the one or more measured parameters comprises at least one of a principal diffusion component-based parameter, a minicolumn-based parameter, or a diffusion-based parameter.

2. The computer-implemented method of claim 1, wherein determining the position in the common space of each of the transformed reference and test points further comprises determining respective sets of reference coordinates and test coordinates for the transformed reference points and test points.

3. The computer-implemented method of claim 2, wherein calculating the displacement of each of the transformed test points relative to each of the transformed reference points further comprises calculating an offset between each set of test coordinates and each set of reference coordinates.

4. The computer-implemented method of claim 2, wherein determining the correspondence between one of the transformed test points and the given transformed reference point further comprises determining the set of test coordinates having a minimum offset relative to the set of reference coordinates of the given transformed reference point.

5. The computer-implemented method of claim 2, wherein the set of reference coordinates and the set of test coordinates comprise at least one of Cartesian coordinates or radial coordinates.

6. The computer-implemented method of claim 1, further comprising comparing the one or more reference values at the given reference point to the one or more test values obtained at the corresponding test point.

7. The computer-implemented method of claim 1, wherein the principal diffusion component-based parameter comprises at least one of an angle of deviation between a principal diffusion direction and a columnar direction of a vertical column through a cortical layer of the brain, perpendicular diffusivity or parallel diffusivity, the minicolumn-based parameter comprises at least one of a minicolumn width, a minicolumn spacing, an axonal fibre bundle width, an axonal fibre bundle spacing, a dendritic fibre bundle width, a dendritic fibre bundle spacing, a minicolumn core width, or minicolumn peripheral neuropil space, and the diffusion-based parameter comprises at least one of mean minicolumn diffusivity, radial diffusivity, fractional anisotropy, mean diffusivity or axial diffusivity.

8. The computer-implemented method of claim 6, further comprising obtaining an indication of a prognosis of at least one disorder in the test brain based on the comparison of the one or more reference values at the given reference point to the one or more test values obtained at the corresponding test point.

9. The computer-implemented method of claim 6, further comprising detecting an indication of a presence of at least one disorder in the test brain based on the comparison of the one or more reference values at the given reference point to the one or more test values obtained at the corresponding test point.

10. The computer-implemented method of claim 9, wherein the at least one disorder comprises a neurodegenerative disorder, a neuroinflammatory disorder, a neurodevelopmental disorder, a psychiatric disorder, or a brain disorder associated with a SARS-CoV-2 infection.

11. The computer-implemented method of claim 8, wherein the at least one disorder comprises Alzheimer's Disease, cerebrovascular dementia, mild cognitive impairment, frontotemporal dementia, dementia with Lewy Bodies, autism, an autism spectrum disorder, multiple sclerosis, epilepsy, amyotrophic lateral sclerosis, Parkinson's disease, schizophrenia, bipolar disorder, dyslexia, Down's syndrome, Huntington's disease, prion disease, depression, obsessive-compulsive disorder, attention deficit hyperactivity disorder, or chronic traumatic encephalopathy.

12. The computer-implemented method of claim 6, further comprising detecting an indication of at least one injury in the test brain based on the comparison of the one or more reference values at the given reference point to the one or more test values obtained at the corresponding test point.

13. The computer-implemented method of claim 12, wherein the at least one injury comprises a mild traumatic brain injury, a concussion, a cerebral contusion, an anoxic brain injury, or a hypoxic brain injury.

14. The computer-implemented method of claim 6, further comprising determining a measure of brain health in the test brain based on the comparison of the one or more reference values at the given reference point to the one or more test values obtained at the corresponding test point.

15. The computer-implemented method of claim 8, further comprising determining at least one therapeutic to be administered based on the obtained indication of the prognosis of at least one disorder in the test brain, the presence of at least one disorder in the test brain, the detected indication of at least one injury in the test brain and/or the determined measure of brain health in the test brain.

16. The computer-implemented method of claim 8, further comprising determining at least one non-pharmacological treatment to be implemented based on the obtained indication of the prognosis of at least one disorder in the test brain, the detected indication of the presence of at least one disorder in the test brain, the detected indication of at least one injury in the test brain and/or the determined measure of brain health in the test brain.

17. The computer-implemented method of claim 1, wherein the at least one image of the reference brain comprises at least one of a brain atlas, an image of a control brain or a second image of the test brain, wherein the control brain comprises a different brain to the test brain.

18. The computer-implemented method of claim 1, wherein the common space is a substantially spherical space.

19. The computer-implemented method of claim 1, wherein the reference points and the test points comprise grey matter surface vertices.

20. The computer-implemented method of claim 1, wherein each of the plurality of reference points is representative of a known marker in the reference brain, and each of the plurality of test points is representative of a known marker in the test brain.

21. A system comprising:

at least one processor; and memory storing computer-executable instructions that, when executed by the at least one processor, cause the at least one processor to:

transform, into a common space, a plurality of reference points obtained from at least one image of a reference brain in a first space wherein each of the reference points comprise a plurality of surface vertices, each associated with a vertex index;

transform, into the common space, a plurality of test points obtained from at least one image of a test brain in a second space wherein each of the test points comprise a plurality of surface vertices, each associated with a surface index;

determine a position of each of the transformed reference points and each of the transformed test points in the common space;

calculate a displacement of each of the transformed test points relative to each of the transformed reference points based on the determined positions;

determine a correspondence between one of the transformed test points and a given transformed reference point based on the calculated displacements, wherein determining the correspondence between one of the transformed test points and the given transformed reference point further comprises determining the transformed test point having a minimum displacement relative to the given transformed reference point;

determine a corresponding test point in the second space to a given reference point in the first space based on the determined correspondence, obtain one or more reference values of one or more measured parameters at each of the plurality of reference points; and obtain corresponding one or more test values of one or more measured parameters at each of the plurality of test points, wherein the one or more measured parameters comprises at least one of a principal diffusion component-based parameter, a minicolumn-based parameter, or a diffusion-based parameter.

22. A computer program product comprising instructions which, when the program is executed by a computer, cause the computer to carry out the method of claim 1.

23. A computer-readable medium comprising instructions which, when executed by a computer, cause the computer to carry out the method of claim 1.

24. A method of treatment comprising:

performing the method according to claim 15 and thereby determining that at least one therapeutic is to be administered; and administering said at least one therapeutic.

25. The method of treatment of claim 24, wherein the at least one therapeutic comprises a small molecule drug, a biologic, or a polynucleotide delivered by a vector or a particle.

26. The method of treatment of claim 24, wherein the at least one disorder comprises Alzheimer's disease and the at least one therapeutic comprises a cholinesterase inhibitor, an N-methyl-D-aspartate antagonist, or a monoclonal antibody, or wherein the at least one disorder comprises Parkinson's disease and the at least one therapeutic comprises a central nervous system agent, a decarboxylase inhibitor, a dopamine agonist, a monoamine oxidase-B inhibitor, a catechol-O-methyltransferase inhibitor, or an adamantane.

27. A method of treatment comprising:

performing the method according to claim 19 and thereby determining that at least one non-pharmacological treatment is to be implemented; and implementing said at least one non-pharmacological treatment.

28. The method of treatment of claim 27, wherein the at least one disorder comprises Alzheimer's disease and the at least one non-pharmacological treatment comprises cognitive stimulation therapy, cognitive rehabilitation, or cognitive behavioural therapy, or wherein the at least one disorder comprises Parkinson's disease and the at least one non-pharmacological treatments comprises physiotherapy, speech and language therapy, deep brain stimulation, or occupational therapy.

29. A computer-implemented method comprising:

transforming, into a common space, a plurality of reference points obtained from at least one image of a reference brain in a first space, wherein each of the reference points are associated with a relative reference position in the first space and comprise a plurality of surface vertices each associated with a vertex index;

transforming, into the common space, a plurality of test points obtained from at least one image of a test brain in a second space, wherein each of the test points are associated with a relative test position in the second space and comprise a plurality of test vertices each associated with a test index;

determining a position of each of the transformed reference points and each of the transformed test points in the common space;

calculating a displacement of each of the transformed test points relative to each of the transformed reference points based on the determined positions;

determining a correspondence between one of the transformed test points and a given transformed reference point based on the calculated displacements;

determining a corresponding test point in the second space to a given reference point in the first space based on the determined correspondence, wherein the relative test position and the relative reference position are substantially equivalent points in the test brain and the reference brain;

obtaining one or more reference values of one or more measured parameters at each of the plurality of reference points;

obtaining corresponding one or more test values of one or more measured parameters at each of the plurality of test points;

comparing the one or more reference values at the given reference point to the one or more test values obtained at the corresponding test point; and obtaining an indication of a prognosis of at least one disorder in the test brain and/or an indication of a presence of at least one disorder in the test brain based on the comparison of the one or more reference values at the given reference point to the one or more test values obtained at the corresponding test point.

* * * * *